(12) United States Patent
Kwon et al.

(10) Patent No.: US 11,987,693 B2
(45) Date of Patent: May 21, 2024

(54) BIOCHEMICAL CARRIERS CAPABLE OF STORAGE, PRESERVATION AND INDEXING AND METHOD FOR FABRICATING THE SAME

(71) Applicants: SEOUL NATIONAL UNIVERSITY R&DB FOUNDATION, Seoul (KR); UNIVERSITY-INDUSTRY COOPERATION GROUP OF KYUNG HEE UNIVERSITY, Yongin-si (KR)

(72) Inventors: Sung Hoon Kwon, Seoul (KR); Wook Park, Yongin-si (KR); Yeong Jae Choi, Seoul (KR); Hyung Jong Bae, Seoul (KR); Tae Hoon Ryu, Seoul (KR); Suk Heung Song, Yongin-si (KR)

(73) Assignees: SEOUL NATIONAL UNIVERSITY R&DB FOUNDATION, Seoul (KR); UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 1443 days.

(21) Appl. No.: 16/335,296

(22) PCT Filed: Oct. 10, 2017

(86) PCT No.: PCT/KR2017/011121
§ 371 (c)(1),
(2) Date: Dec. 9, 2019

(87) PCT Pub. No.: WO2018/066975
PCT Pub. Date: Apr. 12, 2018

(65) Prior Publication Data
US 2020/0143909 A1 May 7, 2020

(30) Foreign Application Priority Data

Oct. 5, 2016 (KR) .................. 10-2016-0128414

(51) Int. Cl.
*G06F 16/22* (2019.01)
*C08J 3/12* (2006.01)
(Continued)

(52) U.S. Cl.
CPC ............... *C08L 35/02* (2013.01); *C08J 3/128* (2013.01); *C08J 9/286* (2013.01); *C12N 15/11* (2013.01);
(Continued)

(58) Field of Classification Search
CPC ...... G01N 33/53; C08L 35/02; G06F 16/2237
(Continued)

(56) References Cited

U.S. PATENT DOCUMENTS 6,093,302 A 7/2000 Montgomery
7,709,544 B2 5/2010 Doyle et al.
(Continued)

FOREIGN PATENT DOCUMENTS

KR 1020100029613 A 3/2010
KR 100966683 B1 6/2010
(Continued)

OTHER PUBLICATIONS

International Search Report of PCT/KR2017/011121, dated Jan. 17, 2018, English translation.
(Continued)

*Primary Examiner* — Ricky Go
(74) *Attorney, Agent, or Firm* — STIP Law Group, LLC

(57) ABSTRACT

Biochemical carriers are provided. Each of the biochemical carriers includes: biochemical molecules having a sequence
(Continued)

into which digital data information is encoded; a carrier particle composed of a polymer matrix and in which the biochemical molecules are connected to the surface or inside of the polymer matrix; and an index code introduced into the carrier particle. Also provided is a method for fabricating biochemical carriers. The fabrication method includes: encoding digital data into a sequence of biochemical molecules; synthesizing the biochemical molecules based on the encoded sequence; mixing the biochemical molecules with a photocurable material; curing the mixture to obtain carrier particles including a polymer matrix; and introducing an index code into the carrier particles simultaneously with or separately from the curing. Also provided is a method for restoring digital data from the biochemical carrier. The restoration method includes: analyzing the index code of the biochemical carrier; reacquiring the biochemical molecules from the biochemical carrier based on the analytical results of the index code; sequencing the biochemical molecules; and decoding the sequencing results to restore digital data.

18 Claims, 15 Drawing Sheets

Specification includes a Sequence Listing.

(51) Int. Cl.
*C08J 9/28* (2006.01)
*C08L 35/02* (2006.01)
*C12N 15/11* (2006.01)

(52) U.S. Cl.
CPC ..... *G06F 16/2237* (2019.01); *C08J 2201/046* (2013.01); *C08J 2333/08* (2013.01); *C08J 2335/02* (2013.01); *C08J 2489/00* (2013.01)

(58) Field of Classification Search
USPC .......................................................... 702/27
See application file for complete search history.

(56) References Cited

U.S. PATENT DOCUMENTS

| 2005/0026181 A1* | 2/2005 | Davis | C12Q 1/6876 435/6.13 |
| 2006/0223126 A1* | 10/2006 | Tamori | G01N 33/5434 435/7.5 |
| 2007/0248957 A1* | 10/2007 | Nova | B82Y 10/00 435/7.1 |
| 2013/0090260 A1* | 4/2013 | Nova | B01L 3/5027 506/37 |

FOREIGN PATENT DOCUMENTS

| KR | 101004769 B1 | 1/2011 |
| KR | 1020130115581 A | 10/2013 |
| KR | 1020150048541 A | 5/2015 |
| KR | 1020150141165 A | 12/2015 |
| KR | 1020160100049 A | 8/2016 |

OTHER PUBLICATIONS

A. P. Blanchard, R. J. Kaiser & L. E. Hood, High-density oligonucleotide arrays, Biosensors & Bioelectronics, 1996, pp. 687-690, vol. 11, No. 6/7, Elsevier Science Ltd, Amsterdam, Netherlands.
Stephen P. A. Fodor et al, Light-Directed, Spatially Addressable Parallel Chemical Synthesis, Science Research article, Feb. 15, 1991, pp. 767-773, American Association for the Advancement of Science, Washington DC, USA.
Mark Schena et al, Quantitative Monitoring of Gene Expression Patterns with a Complementary DNA Microarray, Science, Oct. 20, 1995, vol. 270, No. 5235, pp. 467-470, American Association for the Advancement of Science, Washington DC, USA.
Haohao Lin et al, Replication of a DNA Microarray, JACS Communications, Jul. 23, 2005. vol. 127, No. 32, pp. 11210-11211, American Chemical Society, Washington DC, USA.
Haohao Lin et al, Replication of DNA Microarrays from Zip Code Masters, JACS Communications, Feb. 18, 2006, vol. 128, No. 10, pp. 3268-3272, American Chemical Society, Washington DC, USA.
Robert N. Grass et al, Robust Chemical Preservation of Digital Information on DNA in Silica with Error-Correcting Codes, Angewandte Chem International Edition, 2015, vol. 54, pp. 1-5, Wiley-VCH Verlag GmbH & Co. KGaA, Weinheim, Germany.

* cited by examiner

FIG. 8
| Sample No. | Porogen | | PEGDA700 | Pore size (nm) | Porosity (%) | Bulk density (g/cm³) | remark |
|---|---|---|---|---|---|---|---|
| 1 | PEG1500 | 40% | 20% | 279 | 54.3 | 0.52 | Note) |
| 2 | | 30% | 30% | 140 | 37.1 | 0.73 | • 5% of initiator and 35% of deionized water in common |
| 3 | | 20% | 40% | 88 | 28.0 | 0.83 | |
| 4 | PEG1000 | 40% | 20% | 235 | 49.8 | 0.57 | • Bulk density: density of sample containing pores (reference = water) |
| 5 | | 30% | 30% | 81 | 27.1 | 0.63 | |
| 6 | | 20% | 40% | 51 | 17.6 | 0.99 | • ρ_{H2O} water = 1 (g/cm³) |
| 7 | PEG600 | 40% | 20% | 87 | 25.2 | 0.65 | |
| 8 | | 30% | 30% | 56 | 20.7 | 0.96 | |
| 9 | | 20% | 40% | 29 | 10.9 | 1.05 | |
| 10 | control | 0% | 95% | 22 | 8.9 | 1.11 | 5% of initiator |
FIG. 9(a)
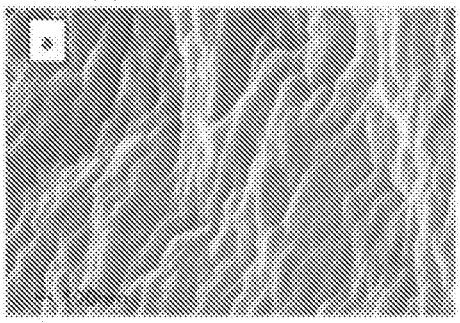
FIG. 9(b)
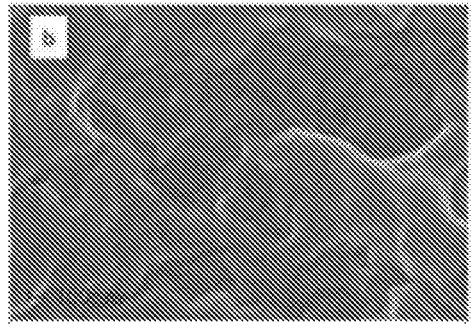

Number of reads acquired

Hunmin.jpeg

Jikji.jpeg

Daedonyeo.jpeg

FIG. 15

```
                                    description.txt

Total 6200 DNA fragment

ENCODEDDATE     FILENAM  NUMBEROFDNAFRAGMENTS   ERRORCORRECTION  FORWARDPRIME      REVERSEPRIMER
Jun 21 17:00    Daedongyeo.jpeg   7208    RS    TAATACGACTCACTATAGGG   TGTGACCTGATCCGC
Jun 21 17:00    jikji.jpeg        7217    RS    ATTTAGGTGACACTATAG     TGTGACCTGATCCGC
Jun 21 17:00    Hunmin.jpeg       6874    RS    GCTAGTTATTGCTCAGCGG    TGTGACCTGATCCGC
```

Daedongyeojido
Daedongyeojido (also Daedong yeojido, Korean:            , lit. "The Great Map of the East Land") is a large scale map of Korea produced by Joseon dynasty cartographer and geologist Kim Jeong-ho in 1861. A second edition was printed in 1864. One source describes it as the "oldest map in Korea". Daedongyeojido is considered very advanced for its time, and marks the zenith of pre-modern Korean cartography.
Jikji
Jikji is the abbreviated title of a Korean Buddhist document, whose title can be translated "Anthology of Great Buddhist Priests' Zen Teachings". Printed during the Goryeo Dynasty in 1377, it is the world's oldest extant book printed with movable metal type. UNESCO confirmed Jikji as the world's oldest metalloid type in September 2001 and includes it in the Memory of the World Programme.
Jikji was published in Heungdeok Temple in 1377, 78 years prior to Johannes Gutenberg's acclaimed "42-Line Bible" printed during the years 1452-1455. The greater part of the Jikji is now lost, and today only the last volume survives, and is kept at the Manuscrits Orientaux division of the National Library of France.
Hunmin
Hunminjeongeum is a document describing an entirely new and native script for the Korean language. The script was initially named after the publication, but later came to be known as hangul. It was created so that the common people illiterate in hanja could accurately and easily read and write the Korean language. It was announced in Volume 102 of the Annals of King Sejong, and its formal supposed publication date, October 9, 1446, is now Hangul Day in South Korea. The Annals place its invention to the 25th year of Sejong's reign, corresponding to 1443-1444.

BIOCHEMICAL CARRIERS CAPABLE OF STORAGE, PRESERVATION AND INDEXING AND METHOD FOR FABRICATING THE SAME

CROSS-REFERENCE TO RELATED APPLICATIONS

This application is the U.S. National Phase under 35 U.S.C. § 371 of International Application No. PCT/KR2017/011121 filed on Oct. 10, 2017, which in turn claims the benefit of Korean Application No. 10-2016-0128414, filed on Oct. 5, 2016, the disclosures of which are incorporated by reference into the present application.

SEQUENCE LISTING

A SEQUENCE LISTING is submitted in a file named PUS190016_ST25.TXT via EFS Web and is hereby incorporated by reference in its entirety. Said file was created on Dec. 6, 2019 and is 57,221 bytes in size.

BACKGROUND OF THE INVENTION

1. Field of the Invention

The present disclosure relates to biochemical carriers and a method for fabricating the same. More specifically, the present invention relates to biochemical carriers that facilitate the storage, preservation, and indexing of a biochemical substance.

2. Description of the Related Art

Biochemical molecules such as nucleic acids and proteins are used for medical and pharmaceutical purposes, including vaccines, therapeutics, and diagnostic probes. Biochemical molecules have recently been used as data storage media in the field of material engineering. To this end, binary digital data represented by 0 and 1 are translated or encoded into sequences of biochemical molecules and are stored. This data storage method has a very high degree of integration and enables information preservation for a very long time without the need for electricity or additional management compared to conventional storage methods.

The introduction of digital data storage in biochemical molecules requires efficient indexing, storage, and handling of the biochemical molecules. Biochemical molecules are featured by the use of very small amounts only once compared to other materials. For example, at most only a few micrograms of biochemical substances such as DNA is used each time for digital data storage and their substantial volume corresponds to a regular tetrahedron with a volume of tens of cubic nanometers. When biochemical molecules are dried or mixed in buffer, they are not individually distinguished from one another. For this reason, users dry or mix biochemical molecules in buffer before storage in a plastic tube or glass bottle with a size of several centimeters. An index can be marked on the surface of the storage container. The index contains the kind of the biochemical molecules, a method for handling the biochemical molecules, a method for reacquiring the biochemical molecules, and a method for decoding the sequence of the biochemical molecules to obtain digital data. However, such an approach uses a larger space than is needed and is thus disadvantageous in terms of integration and efficiency of space utilization. Therefore, there is a need for a technology that can be used to efficiently index, store, and handle biochemical molecules.

SUMMARY OF THE INVENTION

One object of the present invention is to provide biochemical carriers that facilitate the storage, preservation, and indexing of a biochemical substance. A further object of the present invention is to provide a method for fabricating the biochemical carriers.

According to one aspect of the present disclosure, there is provided a biochemical carrier including: biochemical molecules having a sequence into which digital data information is encoded; a carrier particle composed of a polymer matrix and in which the biochemical molecules are connected to the surface or inside of the polymer matrix; and an index code introduced into the carrier particle.

According to a further aspect of the present disclosure, there is provided a method for fabricating biochemical carriers, including: encoding digital data into a sequence of biochemical molecules; synthesizing the biochemical molecules based on the encoded sequence; mixing the biochemical molecules with a photocurable material; curing the mixture to obtain carrier particles including a polymer matrix; introducing an index code into the carrier particles simultaneously with or separately from the curing; and forming protective layers surrounding the carrier particles.

According to another aspect of the present disclosure, there is provided a method for restoring digital data from the biochemical carrier, including: analyzing the index code of the biochemical carrier; reacquiring the biochemical molecules from the biochemical carrier based on the analytical results of the index code; sequencing the biochemical molecules; and decoding the sequencing results to restore digital data.

According to the present disclosure, the biochemical molecules are connected to the encoded porous carrier particles, achieving high integration of space for storage of the biochemical molecules having data information and high stability of the biochemical molecules. The presence of the index code introduced into the carrier particles enables the provision of information about the biochemical molecules in the particles. Therefore, the carriers can be easily be classified, arranged, and handled, eliminating the need for additional classification and arrangement of the carrier particles.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 8 is a table comparing the physical properties of nine samples prepared using three different kinds of porogens with those of a control sample prepared using PEGDA only;

FIG. 15 shows a portion taken from a description of the files shown in FIG. 14.

DETAILED DESCRIPTION OF THE INVENTION

Figure 1A:
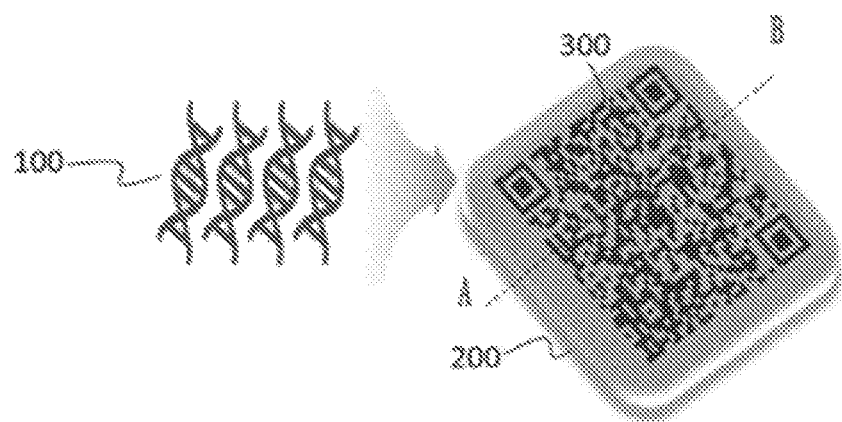
FIGS. 1(a), (b) and (c) show a biochemical carrier according to one embodiment of the present disclosure.

Embodiments of the present disclosure will now be described in more detail with reference to the accompanying drawings. These embodiments are provided so that this disclosure will fully convey the scope of the disclosure to those skilled in the art. Accordingly, the present disclosure may be embodied in many different forms and should not be construed as limited to the exemplary embodiments set forth herein. In the drawings, the dimensions, such as widths, lengths and thicknesses, of elements may be exaggerated for clarity. The same reference numerals refer to the same elements throughout the specification. The drawings are explained from an observer's point of view. It will be understood that when an element is referred to as being "on" another element, it can be directly on the other element, or one or more intervening elements may also be present therebetween.

Figure 1B:
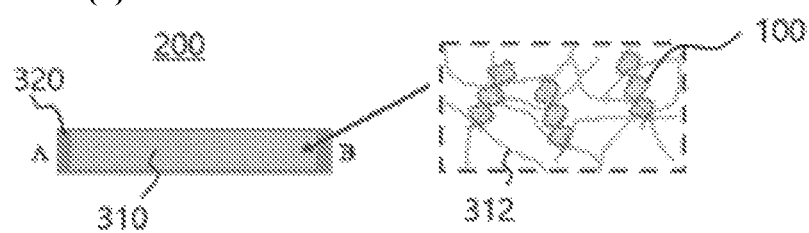
Figure 1C:
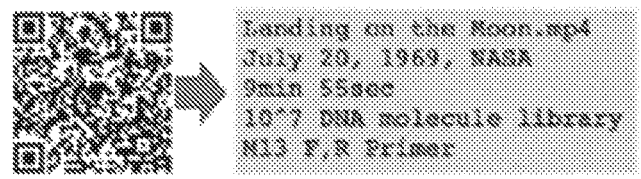

FIG. 1 shows a biochemical carrier according to one embodiment of the present disclosure. In FIG. 1, (a) illustrates an encoded biochemical carrier, (b) is a cross-sectional view taken along line A-B of the encoded biochemical carrier, and (c) illustrates the content of a QR code engraved on the surface of a carrier particle.

The biochemical carrier includes biochemical molecules 100 whose sequence encodes digital data information, a carrier particle 200, and an index code 300. Examples of the biochemical molecules 100 include substances having their own sequences, such as nucleic acids (e.g., DNA and RNA), proteins, antigens, antibodies, Zip nucleic acids (ZNAs), and peptide nucleic acids (PNAs). These substances may be used as a mixture thereof or may be added with chemical substances. The data information may be simple digital data represented by 0 or 1 or book, text, image, picture, number, symbol or code information. For example, the biochemical molecules 100 may be DNA molecules. In this case, binary digital data information represented by 0 and 1 can be converted to quaternary data corresponding to four nucleic acid bases A, T, C, and G of the biochemical molecules. Specific patterns may be formed on the carrier particle. In this case, specific nucleic acid bases corresponding to the patterns are tabulated, and the patterns are translated and encoded into the corresponding nucleic acid bases of the biochemical molecules. The patterns can be encoded through a suitable algorithm or encoding format. The digital data encoded into the sequence can be restored by decoding based on subsequent sequencing.

The carrier particle 200 includes a body composed of a polymer matrix 310. The biochemical molecules 100 are connected to the surface or inside of the polymer matrix 310. This connection enables storage, preservation or transportation of the biochemical molecules 100. Referring to (b) of FIG. 1, the biochemical molecules 100 are physically or chemically connected to and support by the polymer chains of the polymer matrix 310. For connection between the biochemical molecules 100 and the polymer chains 312, the biochemical molecules 100 or the polymer chains 312 may have chemical functional groups at the ends thereof. The chemical functional groups can induce chemical bonds such as ester, ether or amide bonds.

The polymer matrix 310 may be composed of a photocurable polymer. Preferred materials for the polymer matrix 310 are hydrogels that are not dissolved in aqueous environments and have the ability to contain water, thus being suitable for enzymatic and chemical reactions. Hydrogels may have various chemical compositions and physical properties because they can be prepared from various polymers. More preferably, the polymer matrix 310 is made of a porous hydrogel. As will be described below, the porous hydrogel can be prepared by photocuring a mixture containing a photocurable material and an initiator. A non-photocurable material such as polyethylene glycol (PEG) may be optionally added to the mixture during photocuring. The porosity of the polymer matrix 310 can be controlled by varying the size and amount of the biochemical molecules 100 introduced into the polymer matrix 310. That is, the surface area of the carrier particle 200 can be increased such that the largest possible amount of the biochemical molecules 100 is introduced into the smallest possible volume of the carrier, enabling subsequent reacquisition of the biochemical molecules 100 through rapid chemical and biological reactions. The polymer matrix 310 is preferably porous such that the biochemical molecules 100 are easily released from the polymer matrix 310 of the carrier particle 200.

The porosity of the polymer matrix 310 is adjusted such that the average pore size is from 10 to 300 nm, preferably from 10 to 200 nm, more preferably from 20 to 100 nm. The porosity is in the range of 10 to 70%, preferably 20 to 60%. Within this range, a sufficient internal surface area of the polymer matrix 310 can be ensured. The pore size and porosity of the polymer matrix 310 can be appropriately controlled depending on the mechanical properties of the carrier particle 200 and the desired amount of information stored in the carrier particle 200.

A protective layer 320 surrounding the polymer matrix 310 may be introduced into the carrier particle 200. The protective layer 320 may be formed using an inorganic material. Examples of such inorganic materials include: metals such as gold, silver, copper, platinum, iron, and aluminum; and metal oxides such as titania, zirconia, alumina, and silica. Silica is preferred in terms of ease of coating and durability. The protective layer 320 may have a thickness of tens of nanometers to several micrometers. Due to the presence of the protective layer 320, the biochemical molecules 100 can be protected from exposure to external environmental factors such as moisture, heat, and chemicals and the ability of the carrier particle 200 to preserve the biochemical molecules 100 can be markedly improved.

The carrier particle 200 including the polymer matrix body 310 is flexible, soft, and easy to fabricate into various structures and shapes, but it can be easily damaged, either mechanically or chemically. Also, small foreign molecules may be absorbed into the polymer matrix 310 to damage or contaminate the biochemical molecules 100. In contrast, inorganic materials such as titania and silica are typically much harder and have better chemical resistance than organic polymers but tend to be brittle and are difficult to mold into various structures. Therefore, coating of the polymer matrix 310 with an inorganic material could yield a combination of the advantages of the two materials, making the carrier particle 200 hard, tough, chemically stable, highly durable, and easy to mold into various shapes.

In one embodiment, the size of the carrier particle 200 may be determined depending on the amount of the biochemical molecules 100 to be stored. The size of the carrier particle 200 is not particularly limited and may be typically from 1 µm to 1 mm. The carrier particle 200 may have a volume of about $10^{-9}$ to 1 $mm^3$. Thus, the carrier particle 200 can be easily discerned or handled with simple tools such as tweezers and can be observed using a cell phone camera or microscope, unlike nanoscale particles. When the carrier particle 200 has a size suitable for the amount of the biochemical molecules to be stored, space efficiency and convenience can be maximized.

The index code 300 is formed in a portion of the carrier particle 200 to store information about the biochemical molecules 100 connected to the carrier particle 200 and to provide the stored information to users, enabling indexing of the biochemical molecules 100. Referring to (c) of FIG. 1, the index code 300 of the biochemical carrier may be represented by a QR code. The index code 300 may also be represented by a simple binary code consisting of zeros and ones or a graphical code such as a figure. Alternatively, the index code 300 may be represented by fluorescence using a fluorescent dye or bleaching or structural colors using magnetic nanoparticles. Alternatively, the index code 300 may be a spectral code based on photoluminescence using rare earth ion-doped upconversion nanocrystals or quantum dots or a topographical code such as a crease pattern.

The index code 300 may contain information about the biochemical molecules 100 bound to the carrier particle 200, a method for reacquiring and analyzing the biochemical molecules to decode encoded digital information, and a method for accessing to the decoding method.

Specifically, the information about the biochemical molecules 100 may include the kind and amount of the substance, the place where the substance is used, the time when the substance is produced, and how to produce the substance. Thus, when the index code 300 is checked later, the biochemical molecules 100 stored in the carrier particle 200 can be indexed. That is, a user can accurately determine the information stored in the biochemical molecules 100 by decoding the index code 300.

In one embodiment, the index code 300 may include information about a method for reacquiring the biochemical molecules 100. For the reacquisition of the biochemical molecules 100, the connection between the porous polymer matrix 310 and the biochemical molecules 100 needs to be disconnected. Various processes can be employed to disconnect the biochemical molecules 100 from the porous polymer matrix 310. However, an improper disconnection from the porous polymer matrix 310 may lead to damage to the biochemical molecules. The biochemical molecules 100 may be double-stranded DNA molecules. In this case, single-stranded DNA can be reacquired by heating. However, heating for the reacquisition of proteins may lead to denaturation of the proteins. Accordingly, the storage of a reacquisition method suitable for the kind of the biochemical molecules 100 and the connection mode of the biochemical molecules 100 in the index code 300 enables safe reacquisition of the biochemical molecules 100.

Examples of approaches for reacquiring the biochemical molecules 100 include cleavage of chemical bonds in the biochemical molecules 100 by heating the biochemical carrier, irradiating with light in a specific wavelength range or treating with a specific chemical, and enzymatic amplification of the biochemical molecules 100.

In one embodiment, the index code 300 may include a method for removing the protective layer 320, for example, a silica or metal protective layer, as information about the reacquisition of the biochemical molecules 100. Generally, the protective layer 320 can be removed by treatment with a suitable reagent such as an acid. The kind of the reagent, the pH of the acid, and the treatment time may vary depending on the thickness of the protective layer 320. Accordingly, the index code 300 can explicitly specify appropriate treatment conditions to protect the biochemical molecules 100 in the carrier particle 200 from damage by treatment with the reagent in a larger amount than is needed.

Figure 2:
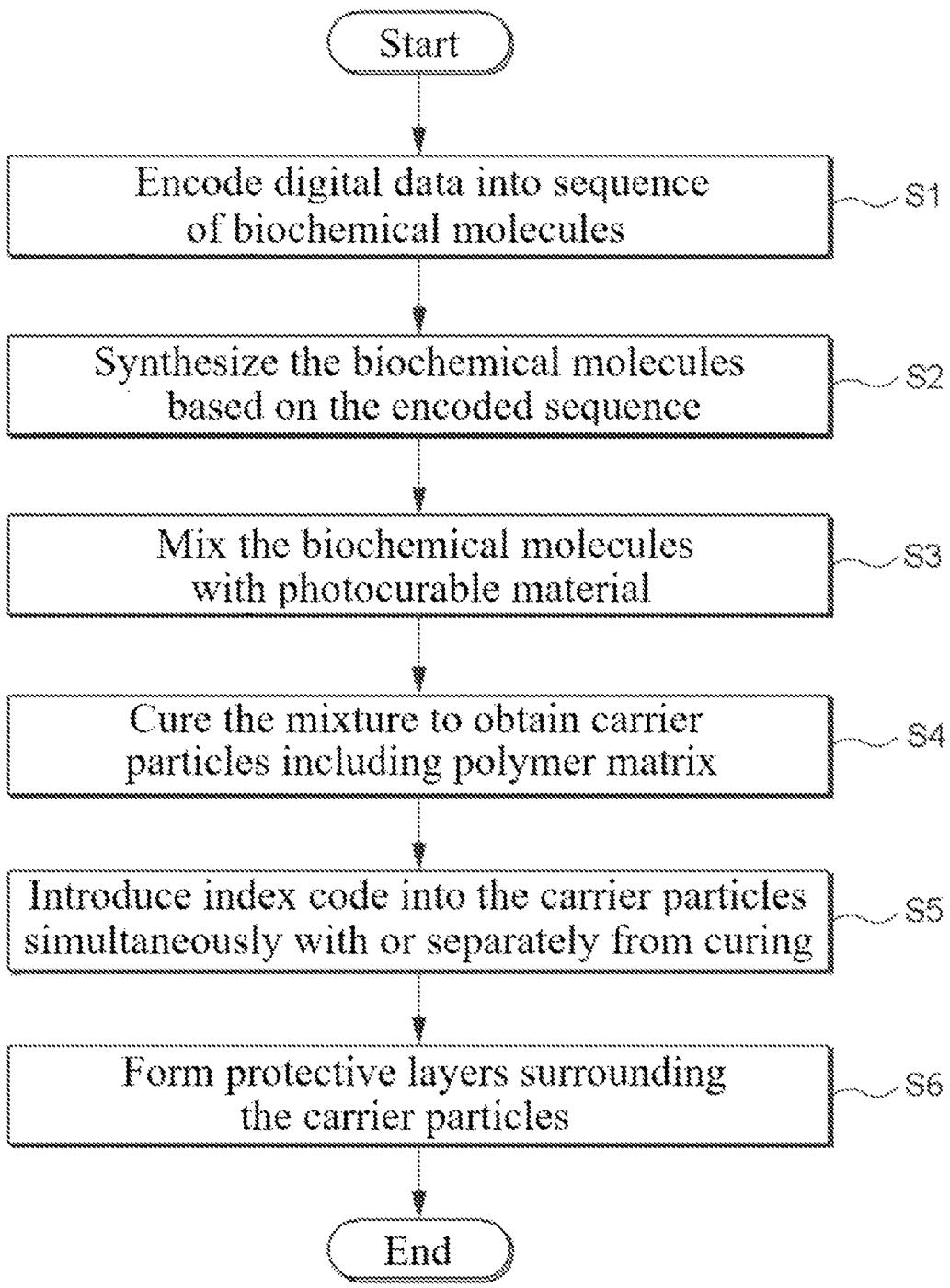
FIG. 2 is a flowchart illustrating a method for fabricating biochemical carriers according to one embodiment of the present disclosure.

According to one embodiment of the present disclosure, there is provided a method for fabricating biochemical carriers. FIG. 2 is a flowchart illustrating the method for fabricating biochemical carriers. Referring to FIG. 2, first, digital data are encoded into a sequence of biochemical molecules (S1). The digital data may be obtained by conversion from analog data. The digital data may include text, number, symbol, image, audio, and video information.

The digital data correspond to a sequence of biochemical molecules. As described previously, the biochemical molecules may be nucleic acids. In this case, the digital data are converted to quaternary data corresponding to nucleic acid bases of the biochemical molecules. In addition, the digital data can be encoded into the sequence of the biochemical molecules through a specific algorithm or encoding format.

In S2, the biochemical molecules are synthesized based on the encoded sequence. The biochemical molecules can be synthesized by various processes. The encoded sequence may be a nucleic acid or amino acid sequence. DNA or RNA molecules as the biochemical molecules may be synthesized on a silica column or microarray using phosphoramidite chemistry. Here, in situ methods can be used to synthesize the DNA or RNA molecules on a microarray. Examples of such in situ methods include ink-jet printing [A. P. Blanchard et al., High-density oligonucleotide arrays, Biosensors & Bioelectronics 11, 687-690(1996)], photolithography [Stephen P. A. Fodor et al., Light-directed, spatially addressable parallel chemical synthesis, Science 251, 767-773(1991)], and electrochemical methods [Donald D. Montgomery, U.S. Pat. No. 6,093,302, Electrochemical solid phase synthesis]. The microarray can be constructed by spotting [Mark Schena et al., Quantitative monitoring of gene expression patterns with a complementary DNA microarray, Science 270, 467-470(1995)] or large-area transfer or replication [Haohao Lin et al., Replication 21-9 of a DNA microarray, JACS 127, 11210-11211 (2005), Haohao Lin et al., Replication of a DNA microarray from zip code masters, JACS 128, 3268-3272 (2006)]. According to the spotting method, different kinds of molecules are individually stamped on individual spots on a substrate. The biochemical molecules may include proteins, antigens, and antibodies synthesized through enzymatic or chemical reactions of DNA or RNA synthesized by the above methods.

In S3, the biochemical molecules are mixed with a photocurable material. Examples of photocurable materials suitable for use in S3 include ethoxylated trimethylolpropane triacrylate, 2-hydroxyethyl methacrylate, methyl methacrylate, acrylamide, allyl amine, polyethylene oxide, polyethylene glycol diacrylate, polypropylene glycol diacrylate, polyvinylpyrrolidone, polyvinyl alcohol, and polyacrylate. These photocurable materials may be used alone or in combination thereof. For example, polyethylene glycol diacrylate as the photocurable material may be cross-linked into a three-dimensional hydrogel via free radical polymerization due to the presence of acrylate groups at both ends of polyethylene glycol. The photocurable material may be any material that can be changed from a liquid to a solid by external light. Commercially available products of the photocurable material include photoresists such as SU-8 and optical adhesives such as Norland Optical Adhesive (NOA).

The mixture of the biochemical molecules and the photocurable material may further include an initiator. The initiator may induce free radical polymerization of the mixture by an external energy source. The initiator may be an azo-based compound or a peroxide. The mixture may further include a proper cross-linking agent. Examples of such cross-linking agents include N,N'-methylenebisacrylamide, methylenebismethacrylamide, and ethylene glycol dimethacrylate.

The biochemical molecules may have functional groups that are chemically connected to the chains of the polymer matrix to form chemical bonds with the polymer matrix when the polymer matrix is formed by curing the photocurable material. To this end, the biochemical molecules may include chemical functional groups or chemically modified functional groups. For example, DNA molecules as the biochemical molecules may be synthesized according to the digital data information and amplified by polymerase chain reaction (PCR) using primers having acrylamide functional groups. Alternatively, RNA molecules as the biochemical molecules may be added with nucleotides having acrylamide functional groups upon transcription or may be attached with acrylamide functional groups at the ends thereof during their chemical synthesis. The biochemical molecules may be protein molecules. Also in this case, the protein may be added with modified amino acids attached with acrylamide functional groups during their chemical synthesis or may be added with functional groups at the —SH or amine groups thereof through chemical reactions.

In one embodiment, the mixture may further include a porogen. The porogen is a non-photocurable material that does not participate in the curing reaction of the photocurable material.

The porogen forms pores in the matrix to increase the surface area of carrier particles. The presence of the porogen allows the carrier particles to take the form of a porous hydrogel after curing.

The porogen may be used in an amount of 40 to 250 parts by weight, 50 to 200 parts by weight, based on 100 parts by weight of the photocurable material. If the amount of the porogen is less than the lower limit, the porosity of the polymer matrix may not be sufficiently ensured. Meanwhile, if the amount of the porogen exceeds the upper limit, the apparent specific gravity of the carrier particles may be extremely lowered, and as a result, the total amount of the biochemical molecules to be stored may be insufficient. The porogen may be a polyalkylene glycol. The porogen is preferably polyethylene glycol or polypropylene glycol in terms of compatibility with the photocurable material and physical properties. The increased surface area of the polymer matrix enables the connection of the largest possible amount of the biochemical molecules to the smallest possible volume of the carrier particles and can bring about rapid chemical and biological reactions in the subsequent reacquisition of the biochemical molecules.

In S4, the mixture is cured to obtain carrier particles including the polymer matrix. The mixture can be cured by the application of patterned energy thereto. The patterned energy is not limited and may be, for example, ultraviolet light, visible light, infrared light or electron beam. For example, ultraviolet light as the patterned energy may be irradiated through a physical mask or a digital micromirror device (DMD).

The mixture can be cured by various lithography processes. Examples of such lithography processes include general photolithography processes using a contact masks, optofluidic maskless lithography (OFML) using a digital micromirror device, and stop-flow lithography for synthesis in microfluidic channels.

As a result of the curing, easy-to-handle solid carrier particles are obtained. After the curing, the biochemical molecules can be immobilized on the polymer matrix. Particularly, the chemical connection of the biochemical molecules to the polymer matrix through chemical functional groups can minimize the loss of the biochemical molecules against external environmental factors.

In S5, an index code is introduced into the carrier particles simultaneously with or separately from the curing. The encoding can be performed by various processes. In one embodiment, patterning by optical lithography may be applied to encode the carrier particles. For example, the carrier particles may be patterned by various lithography processes known in the art, for example, optofluidic lithography, which is described in Korean Patent No. 1004769, and a combination of flow lithography and polymerization, which is described in U.S. Pat. No. 7,709,544. For example, the carrier particles may be encoded by patterning labels representing '1' and '0' on the photocurable polymer. The labels are distinguished from each other depending on the degree of photocuring. For example, a digital micromirror device using no mask may be employed for optical lithography. In this case, various kinds of codes, for example, as many as one million kinds of codes, can be advantageously formed on the particles including the target sub stance.

In a further embodiment, the encoding of the carrier particles may be achieved by incorporating fluorescent materials with various colors distinguishable from each other into the carrier particles. Various known techniques may be applied to incorporate fluorescent materials into the carrier particles.

In another embodiment, the carrier particles may be encoded by forming color codes using a magnetic ink. For example, a method for forming color codes using a magnetic ink is disclosed in Korean Patent Application No. 10-2010-0029613. According to this method, an external magnetic field is applied to a photocurable material including magnetic nanoparticles to align the magnetic nanoparticles in the photocurable material, and external light is applied to cure the photocurable material. In response to the intensity of the external magnetic field, the array of the magnetic nanoparticles is varied to emit different colors. By the application of such techniques, magnetic nanoparticles can be arranged so as to be distinguished from each other in the carrier particles composed of the photocurable polymer, so that color codes can be formed on the carrier particles. The disclosure of the patent publication is incorporated herein by reference.

The index code may include information about the mixed substance, a method for reacquiring the mixed substance, and a decoding method. In one embodiment, the index code may include URL through which the data information is uploaded to a web server. Thus, a user can access to more data information than the amount of the information about the biochemical molecules stored in the code through the web server whenever necessary.

In S6, protective layers surrounding the carrier particles are formed. The protective layers may continuously surround the surfaces of the carrier particles and may be silica or metal protective layers consisting of Si—O—Si bonds. In the case where the protective layers are silica protective layers, a linker material may be introduced to facilitate the formation of the silica protective layers when the mixture of the photocurable material is cured by optical lithography in S4. Specifically, a linker material having both photocurable functional groups (e.g., acrylate groups) and siloxane bond-forming functional groups (e.g., alkoxysilyl groups) is mixed with the mixture of the photocurable material to produce the carrier particles. Silica protective layers are introduced by subsequent sol-gel reaction with a silica precursor. The linker reacts with the photocurable material to prepare a copolymer as a skeleton of the carrier particles, and at the same time, it allows alkoxysilyl groups to be present on the surfaces of the carrier particles. As a result, the alkoxysilyl groups grafted onto the surfaces of the carrier particles react with the silica precursor to form —Si—O—Si— bonds at the core-shell interfaces. If the carrier particles are composed of the photocurable material alone, silica shells are not easy to form through subsequent silica coating. In contrast, when the mixture of the photocurable material and the linker having functional groups polymerizable with the photocurable material and alkoxysilyl groups is cured as in the method according to the embodiment of the present disclosure, the alkoxysilyl groups are grafted onto the surfaces of the carrier particles, and thereafter, silica shells can be coated on the carrier particles through the alkoxysilyl groups.

The silica shell formation may be performed by various processes known in the art, for example, via a modified Stober method. First, the alkoxysilyl group-grafted carrier particles are added to a solution of distilled water, ethanol, and $NH_4OH$. Next, tetraethylorthosilicate (TEOS) as a silica precursor is injected into the solution to react with the alkoxysilyl groups grafted onto the surfaces of the carrier particles. As a result of the reaction, silica shells are formed and —Si—O—Si— bonds are formed at the core-shell interfaces.

In one embodiment, the protective layers may be formed by metal deposition. The metal deposition can be performed by a sputtering technique. The sputtering technique may be DC sputtering using direct current power and RF sputtering using radio frequency. The metal deposition is preferably performed by DC sputtering. The sputtering technique starts from collision between electrons generated from a gas supplied in a chamber. Electrons are emitted when an inert gas (argon or nitrogen) is filled and a voltage is applied to a cathode. The electrons collide with and ionize the inert gas atoms. The ionized gas is excited to emit electrons and energy, which create a purple plasma in which ions and electrons coexist. The gas and the ions present in the plasma are accelerated toward a metal target as the cathode by a large potential difference. The gas and the ions collide with the surface of the target, and as a result, neutral metal target atoms are ejected from the target surface and deposited on a substrate to form a thin film. The metal protective layers are formed on the surfaces of the carrier particles based on the above-described principle. The metal may be, for example, platinum, gold, silver, copper, iron or aluminum.

Biochemical carriers fabricated by the method may have a size larger than 1 μm and smaller than 1 mm. This size is the smallest unit that can be easily distinguished and handled with simple tools such as tweezers and can be observed using a cell phone camera or microscope, unlike nanoscale particles.

The amount of the digital data per particle of each biochemical carrier can be determined depending on the amount of the biochemical molecules added. Each particle having a size of 500 μm can store several terabytes of data. This storage density is higher than those of current hard disks and SSDs. Since the minimum size of a particle for the storage of data having a specific capacity is dependent on the capacity of the data, the size and shape of the particle can be adjusted to desired levels based on the capacity of the data, if needed.

The biochemical carriers can be stored either individually or as a mixture thereof in a dry state. If needed, the biochemical carriers can be stored in pools by self-assembly on a substrate, microfluidic assembly or interparticle assembly. The biochemical carriers can be dispersed in a suitable solvent such as water, ethanol or buffer before storage in a plastic or glass bottle.

The presence or absence of these particles and their code can be observed with naked eyes or under a low-magnification microscope. Thus, the particles can be easily handled with suitable tools such as tweezers or pipettes. For rapid handling, the particles can be separated by a fluidic particle separation technique based on flow cytometry. Alternatively, the particles may be separated by laser irradiation after drying.

Figure 3:
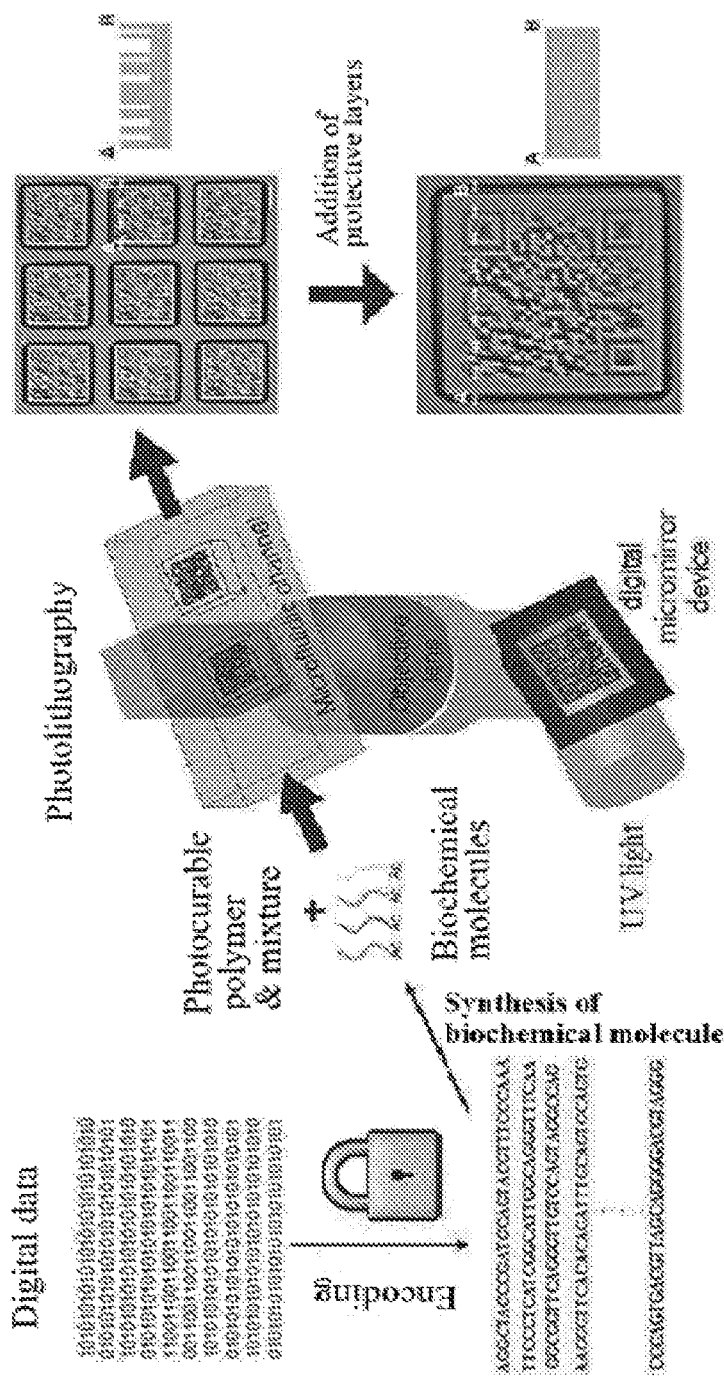
FIG. 3 is a detailed diagram illustrating a method for fabricating biochemical carriers according to one embodiment of the present disclosure.

FIG. 3 is a detailed diagram illustrating a method for fabricating biochemical carriers according to one embodiment of the present disclosure. Referring to FIG. 3, the method includes: encoding digital data consisting of zeros and ones into four nucleic acid bases A, T, C and G; synthesizing biochemical molecules according to the sequence of the nucleic acid bases; mixing the biochemical molecules with a mixture containing a photocurable polymer and subjecting the mixture to photolithography using a digital micromirror device to form carrier particles encoded with information related to the biochemical molecules; and adding a protective layer to each of the carrier particles. The method enables the fabrication of biochemical carriers that have the ability to store, preserve, and index the biochemical molecules. In FIG. 3, the terminal groups Ac of the biochemical molecules represent functional groups capable of chemically bonding with the photocurable polymer.

Figure 4:
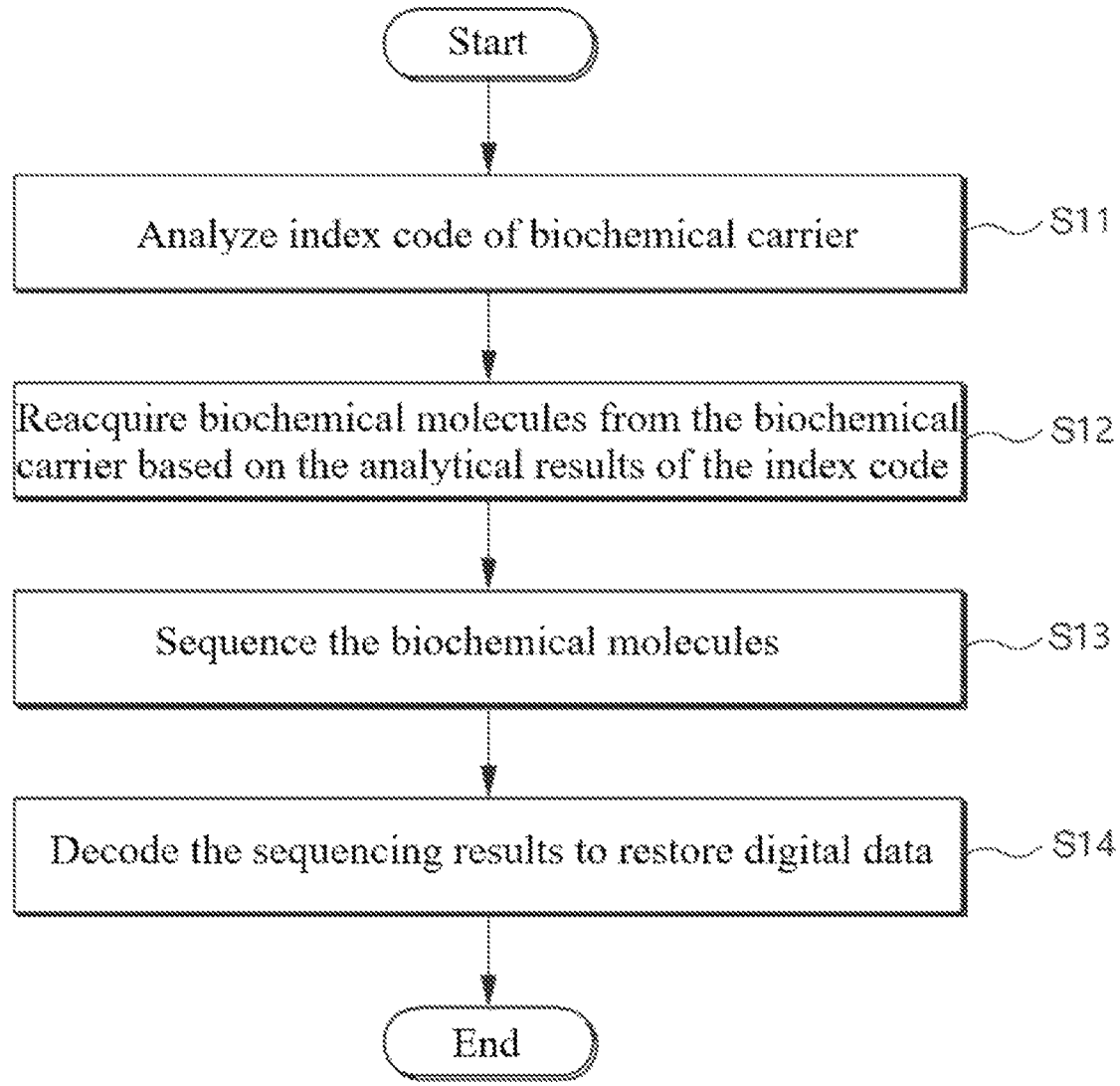
FIG. 4 is a flowchart illustrating a method for restoring digital data according to one embodiment of the present disclosure.

According to one embodiment of the present disclosure, there is provided a method for restoring digital data from the biochemical carriers. FIG. 4 is a flowchart illustrating a method for restoring digital data according to one embodiment of the present disclosure. Referring to FIG. 4, in S11, the index code of the carrier particles into which the biochemical molecules are introduced is analyzed. The index code may contain schematic information including a method for reacquiring the biochemical molecules. Information about the carrier particles can be rapidly obtained using a suitable image analyzer such as a QR code reader.

In S12, the biochemical molecules are reacquired from the carrier particles based on the analytical results of the index code (S12). The biochemical molecules connectively immobilized onto the porous carrier particles can be reacquired in various ways. As an example, DNA molecules as the biochemical molecules may be separated from the carrier particles using a restriction enzyme based on the index code. Alternatively, the DNA molecules may be separated by amplification using a polymerase based on DNA primer information in the index code. As another example, RNA molecules as the biochemical molecules may be separated after transcription into DNA using a reverse transcriptase based on the index code.

As described above, the biochemical molecules acquired without modification of their original form may remain unmodified without substantial loss in their amount in the carrier particles even after reacquisition. The biochemical molecules can be reacquired from the carrier particles due to the ability of the biochemical carriers to store and preserve the biochemical molecules.

The method may optionally further include removing protective layers formed on the carrier particles before reacquisition of the biochemical molecules. The protective layers can be removed by physical or chemical treatment. For example, the protective layers may be removed by treatment with an acidic reagent. The index code may contain information about a method for removing the protective layers.

In S13, the biochemical molecules are sequenced. The biochemical molecules amplified or separated from the carrier particles can be sequenced by appropriate sequencing methods, for example, next-generation sequencing (NGS), Sanger sequencing, and nanopore sequencing.

In S14, the sequencing results are decoded to restore digital data. In one embodiment, the index code may further include a method for translating the sequence of the biochemical molecules that is used to reacquire digital data information. That is, when encoded digital data are encoded and stored, the index code may include information about the encoding format (for example, an encoding algorism or a table showing digital information corresponding to the sequence of the biochemical molecules).

Figure 5:
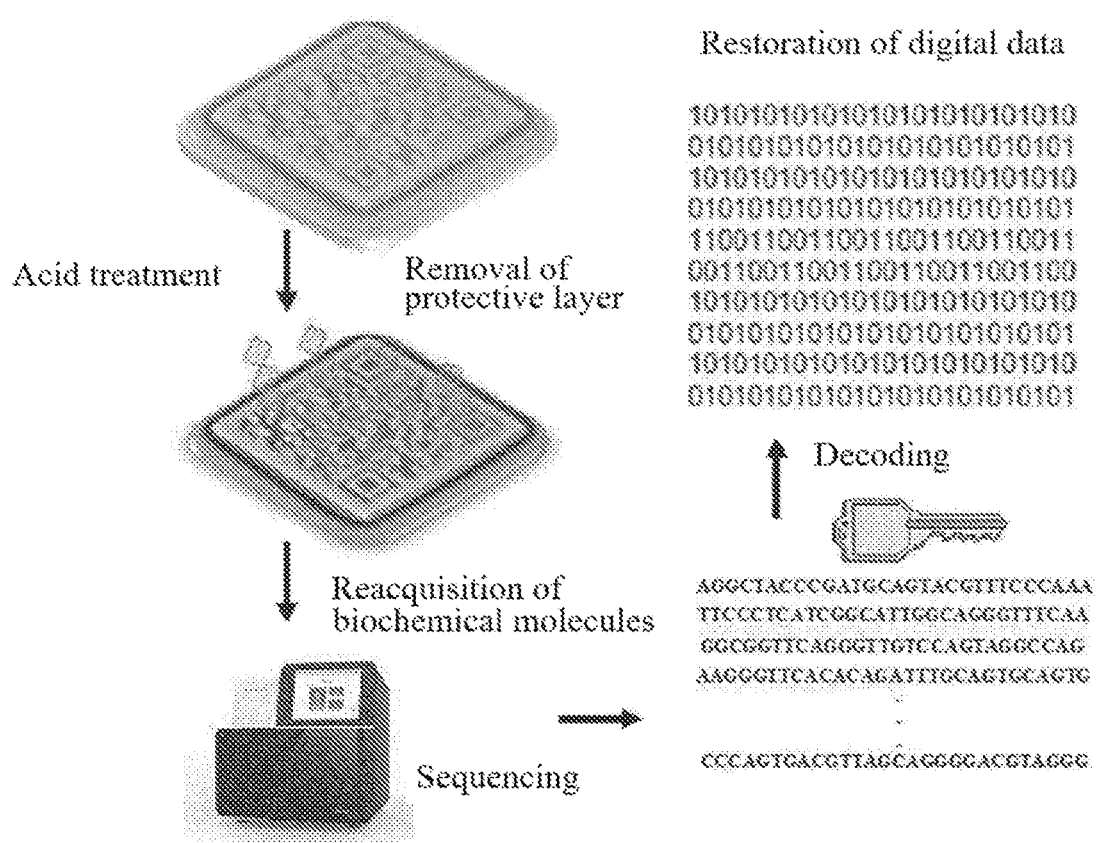
FIG. 5 schematically illustrates a method for restoring digital data from a biochemical carrier according to one embodiment of the present disclosure.
Figure 6A:
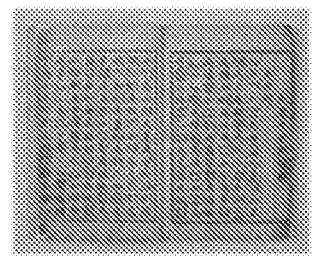
FIGS. 6(a), (b), (c) and (d) show an actual biochemical carrier fabricated by a method according to one embodiment of the present disclosure.
Figure 6B:
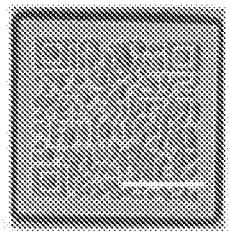
Figure 6C:
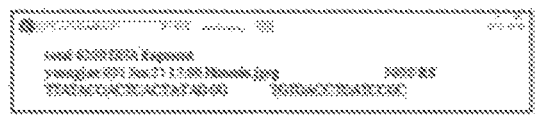
Figure 6D:
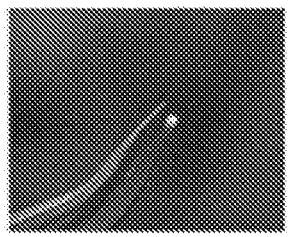

FIG. 5 schematically illustrates a method for restoring digital data from a biochemical carrier according to one embodiment of the present disclosure. Referring to FIG. 5, a protective layer is removed by acid treatment of the biochemical carrier in which digital data are stored in the form of a sequence of biochemical molecules, the biochemical molecules are reacquired from a carrier particle, the biochemical molecules are sequenced to obtain sequence information, and the sequence information is decoded to restore the original digital data.

Based on the ability of the biochemical carriers to preserve the original form of the biochemical molecules, a desired data set can also be selectively recovered from a plurality of data sets stored in each particle. In one embodiment, the carrier particles may include a plurality of data sets. In this embodiment, the biochemical molecule corresponding to one of the plurality of data sets is selected based on the code created in the carrier particles and the selected biochemical molecule is sequenced to selectively restore the desired data set. For selective restoration of the desired data set from the plurality of data sets, a header file or summary file of the data can be stored in the carrier particles. The header file is stored in the form of an index code on the carrier particles. Alternatively, the header file may be stored in the carrier particles after encoding into the sequence of the biochemical molecules. The latter case has the inconvenience that the header file should be decoded before subsequent data recovery. Despite the inconvenience, the latter case can be used when the file has a capacity exceeding the storage limit of the index code on the particles.

As described above, the present disclosure has the advantages of high integration of space for storage of the biochemical molecules carrying data information and high stability of the biochemical molecules because the biochemical molecules are connected to the encoded porous carrier particles. In addition, the index code in the carrier particles can provide information about the biochemical molecules in the particles, and as a result, the carriers are easy to classify, arrange, and handle. Therefore, the need for additional classification and arrangement of the carrier particles can be avoided.

Furthermore, according to the present disclosure, the biochemical molecules connected to the carrier particles are not lost during analysis. This feature is advantageous in maintaining the original form of the highly complex biochemical substance. For example, thousands to hundreds of thousands of digital data are stored in DNA fragments. DNA is generally amplified using a polymerase for replication or analysis. During amplification, however, an imbalance may arise between data components due to different amplification efficiencies of the nucleic acid fragments. This imbalance may become more serious as the amplification proceeds. That is, conventional digital data storage formats using DNA do not retain the original data configuration any further and cannot replicate the original form once the data are analyzed. Such conventional formats can be considered write-once-read-once (WORO) systems.

In contrast, according to the present disclosure, the biochemical substance as an original form can be retained even after amplification using a polymerase because the original form is connectively immobilized on the particles. Although the biochemical substance is adherent to the particles, no influence is given to the function of the biochemical substance to store information because the distal ends of the biochemical substance connected to the carrier particles are not directly involved in amplification.

Moreover, according to the present disclosure, the amount of the original biochemical molecules can be preserved without loss even when the biochemical carriers are reused dozens of times. As a result, the present disclosure can first establish a write-once-read-many (WORM) system as a methodology for storing data in a biochemical substance.

EXAMPLES

1. Fabrication of Biochemical Carriers

Biochemical carriers were fabricated by the following procedure. FIG. 6 shows an actual biochemical carrier fabricated by a method according to one embodiment of the present disclosure. In FIG. 6, (a) is a scanning image of the Haerye edition of Hunminj eongeum, a document describing an entirely new and native script for the Korean language, to be stored in the biochemical carrier, and (b) is an image of a synthesized carrier particle. The scale bar in the bottom right hand corner of the image represents 200 μm. In FIG. 6, (c) shows information determined after recognition of a QR code of the carrier particle and exemplary results when access to the indicated URL, and (d) shows handling of the carrier particle with tweezers.

In this experiment, the first sheet of the Haerye edition of Hunminjeongeum was scanned as digital data information to be stored (see (a) of FIG. 6). The information of the scanned image was designed as about 500 DNA fragments having a length of 150 nucleotides (nt) using the algorithm proposed in R. N. Grass, R. Heckel, M. Puddu, D. Paunescu, W. J. Stark, Angew. Chem. Int. Ed. Engl. 2015, 54, 25525. The DNA fragments were synthesized from microarray oligo pools.

The synthesized DNA was amplified by PCR using primers containing acrylamide groups as pendant chemical groups. The amplification products were mixed with polyethylene glycol diacrylate (PEGDA) as a photocurable material and a photocuring initiator. Thereafter, the mixture was photocured by optofluidic maskless lithography (OFML) to fabricate carrier particles having a size of about 500 μm. A QR code was engraved on the surface of each carrier particle (see (b) of FIG. 6).

Information about the primers and an encoding technique for reacquiring the stored DNA from the carrier particles were included in the QR code. The QR code included URL information related to the information about the carrier particles. When the data information exceeded the information storage capacity of the QR code, a user was allowed to access to the web server where the data information was stored (see (c) of FIG. 6). The particles could be observed with naked eyes and easily handled with tweezers (see (d) of FIG. 6).

qPCR was used to determine whether the amount of digital data stored in each particle varied depending on the amount of DNA added. Each particle was found to have the ability to store several terabytes of data.

2. Test for Optimization of Porous Hydrogel as Material for the Carrier Particles A PEGDA hydrogel as a photocurable material was used to produce polymer matrix bodies of biochemical carriers. Polyethylene glycol as a porogen was added to a mixture containing the photocurable material to fabricate carrier particles composed of a porous hydrogel.

The porosity and average pore size of the carrier particles were measured. DNA present in the carrier particles was amplified by PCR to compare amplification rates between the carrier particles composed of the porous hydrogel and carrier particles composed of a non-porous hydrogel.

Figure 7:
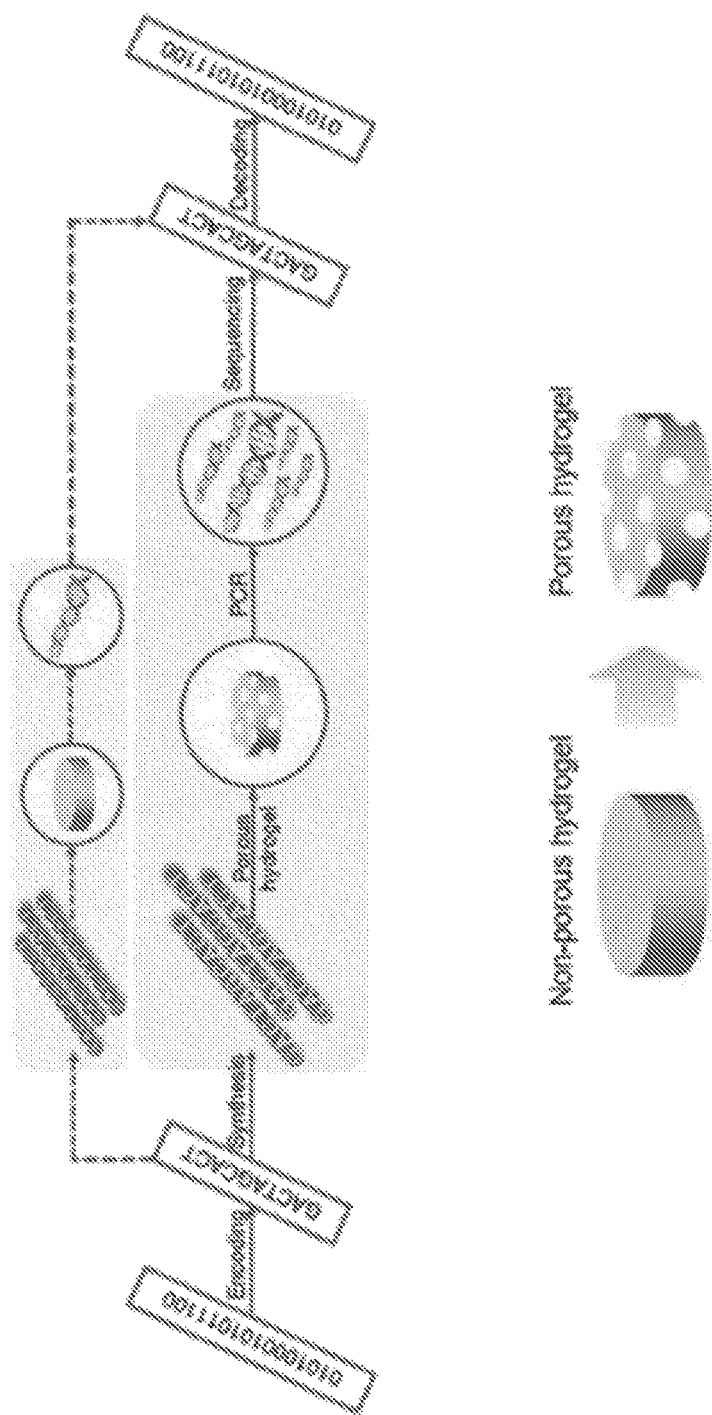
FIG. 7 is a conceptual diagram comparing PCR amplification rates between a particle composed of a nonporous hydrogel and a particle composed of a porous hydrogel.

FIG. 7 is a conceptual diagram comparing PCR amplification rates between a particle composed of a nonporous hydrogel and a particle composed of a porous hydrogel. Referring to FIG. 7, even DNA present in the carrier particle composed of a porous hydrogel can be amplified by PCR due to the increased surface area of the carrier particle, resulting in an increase in PCR efficiency. Even DNA present in a small amount relative to the same volume can be amplified by PCR, resulting in an increase in DNA capacity.

FIG. 8 is a table comparing the physical properties of nine samples prepared using three different kinds of porogens with those of a control sample prepared using PEGDA only. All percentages given in the table represent weight percentages of the raw materials. PEGDA 700 was used as a photocurable material for fabricating carrier particles. PEG 600, PEG 1000, and PEG 1500 were used as porogens. The average pore sizes and porosities were measured by mercury intrusion porosimetry.

Referring to FIG. 8, the pore size increased with increasing PEG content. The samples using PEG 1500 were found to have an average pore size of 170 nm and an average porosity of 40%. The samples using PEG 1000 were found to have an average pore size of 120 nm and an average porosity of 32%. The samples using PEG 600 had an average pore size of 60 nm and an average porosity of 19%. That is, as the degree of polymerization of the used PEG porogen increased, the pore size and porosity increased. In contrast, the control sample using none of the porogens had a pore size of 22 nm and a porosity of ~9%. These results demonstrate that the pore size and porosity of the carrier particles can be controlled by varying the kind and amount of the porogen.

Figure 9C:
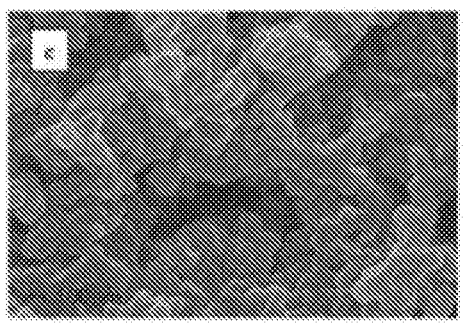
FIGS. 9(a), (b), (c) and (d) show cross-sectional scanning electron microscopy images of carrier particles using PEG 600 as a porogen.
Figure 9D:
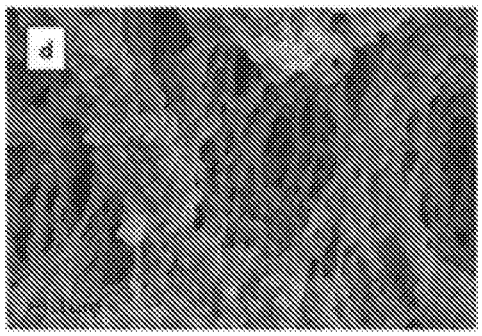

FIG. 9 shows cross-sectional scanning electron microscopy images of carrier particles using PEG 600 as a porogen. In FIG. 9, a is an image of the carrier particle synthesized using PEGDA 700 alone as a control, and b, c, and d are images of the carrier particles synthesized using PEG 600/PEGDA 700 in different ratios of 20/40, 30/30, and 40/20, respectively.

Figure 10A:
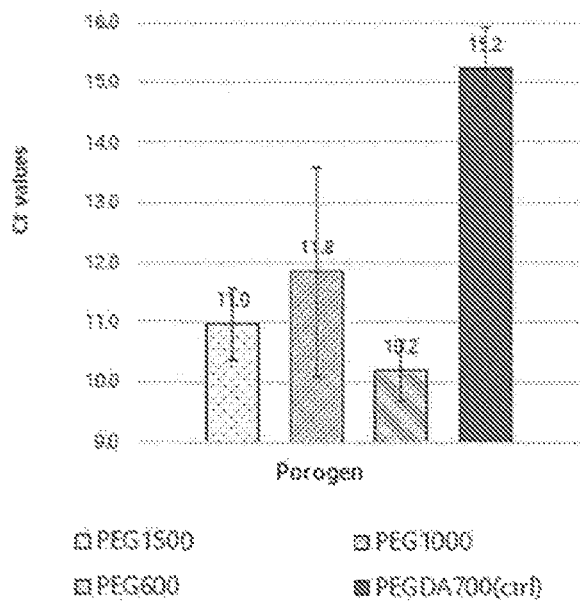
FIGS. 10(a) and (b) compare PCR amplification rates of DNA in carrier particles using different porous hydrogels.
Figure 10B:
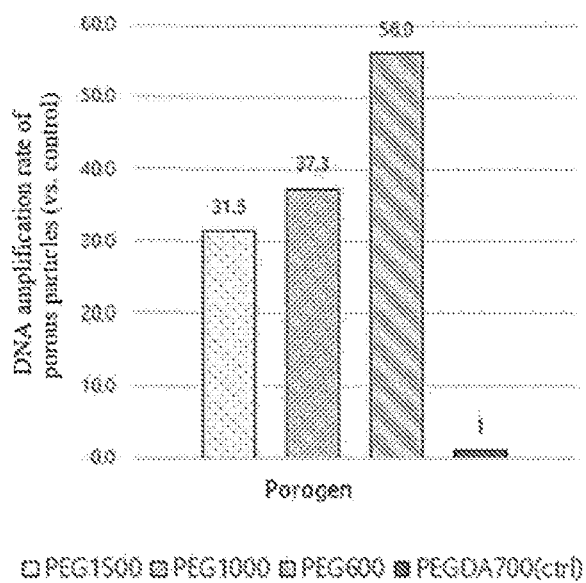

FIG. 10 compares PCR amplification rates of DNA in carrier particles using different porous hydrogels. (a) of FIG. 10 compares Ct values of PCR (cycle numbers when PCR amplification products reach predetermined levels) for a control sample using PEGDA 700 alone and three samples using polyethylene glycol as a porogen (PEGDA 700:PEG 1500=20:40, PEGDA 700:PEG 1000=20:40, PEGDA 700:PEG 600=40:20 (w/w)). (b) of FIG. 10 compares DNA amplification rates of the porous particles with that of the control.

As can be seen from FIG. 10, the carrier particles using the porous hydrogels were more effectively amplified compared to the carrier particles using the general hydrogel due to the presence of a larger number of DNA molecules contributing to the reaction. Particularly, the highest amplification rate was achieved in the carrier particles using PEG 600.

3. Test for Ability of Biochemical Carriers to Preserve Biochemical Molecules in the Presence and Absence of Protective Layers Biochemical carriers were tested for the ability of biochemical carriers to preserve biochemical molecules against an external chemical stimulus in the presence and absence of silica protective layers. For comparison, three samples in the form of microparticles including DNA molecules introduced thereinto were prepared. One of the samples was an untreated control (sample 1) and the other two samples (samples 2 and 3) were subjected to DNA damage by reactive oxygen species (ROS). Silica protective layers were absent in the sample 2. Silica protective layers were present in the sample 3. The silica protective layers were introduced by the following procedure. First, a mixture containing a photocurable material and related additives was mixed with a linker material having siloxane bond-forming functional groups to obtain carrier particles grafted with the siloxane bond-forming functional groups. Thereafter, silica protective layers were formed on the particles by sol-gel reaction with a silica precursor.

Figure 11:
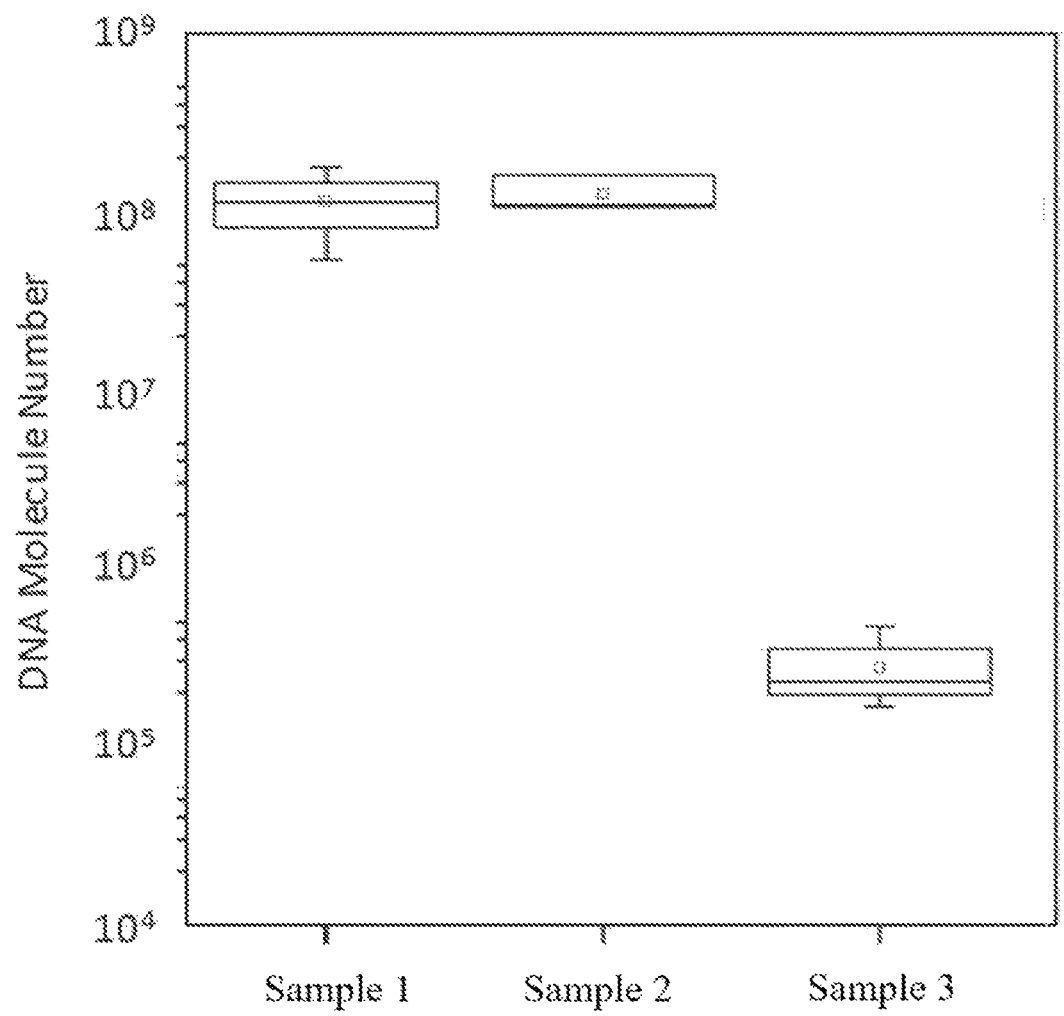
FIG. 11 shows test results of DNA damage by reactive oxygen species (ROS)

FIG. 11 shows test results of DNA damage by reactive oxygen species (ROS). In FIG. 11, the Y-axis represents the samples and the Y-axis represents the number of DNA molecules present on the carrier particles. Referring to FIG. 11, the number of the DNA molecules on the particles having the silica protective layers (sample 3) was maintained unchanged even after exposure to reactive oxygen species, whereas at least 95% of the DNA molecules on the particles without silica protective layers (sample 2) were damaged, which were confirmed by qPCR.

4. Recovery of the Original Data from the Biochemical Carriers

The silica protective layers of the carrier particles were incubated with 400-fold diluted buffered oxide etch (BOE) at room temperature for ~20 min, followed by etching. Any material capable of etching the protective layers may be generally used. For example, hydrofluoric acid can be used instead of BOE. The etching material was diluted as much as possible to avoid an influence on DNA of the carrier particles. Thereafter, the particles were washed several times with Tris-EDTA (pH 7.2) to normalize the pH and BOE was washed out from the filtrate. The acquired carrier particles were transferred to a PCR solution composed of primers having the sequences acquired according to the instructions written in the index code and a DNA polymerase. PCR was performed to amplify the DNA in the particles.

The amplified DNA was sequenced by next-generation sequencing (NGS) to acquire two million paired-end reads, which correspond to an amount such that about 5000 designs can be read 200 times each. The reason why each design is read 200 times is to minimize the loss of the design components caused by the presence of an imbalance between the design components.

After assembly of the paired-end reads, 150 bp long reads were reacquired. The reacquired reads corresponded to 70% of the initial data. The acquired data were allocated to the upstream design configuration addresses to obtain a probability histogram of the acquired reads between the components.

Figure 12:
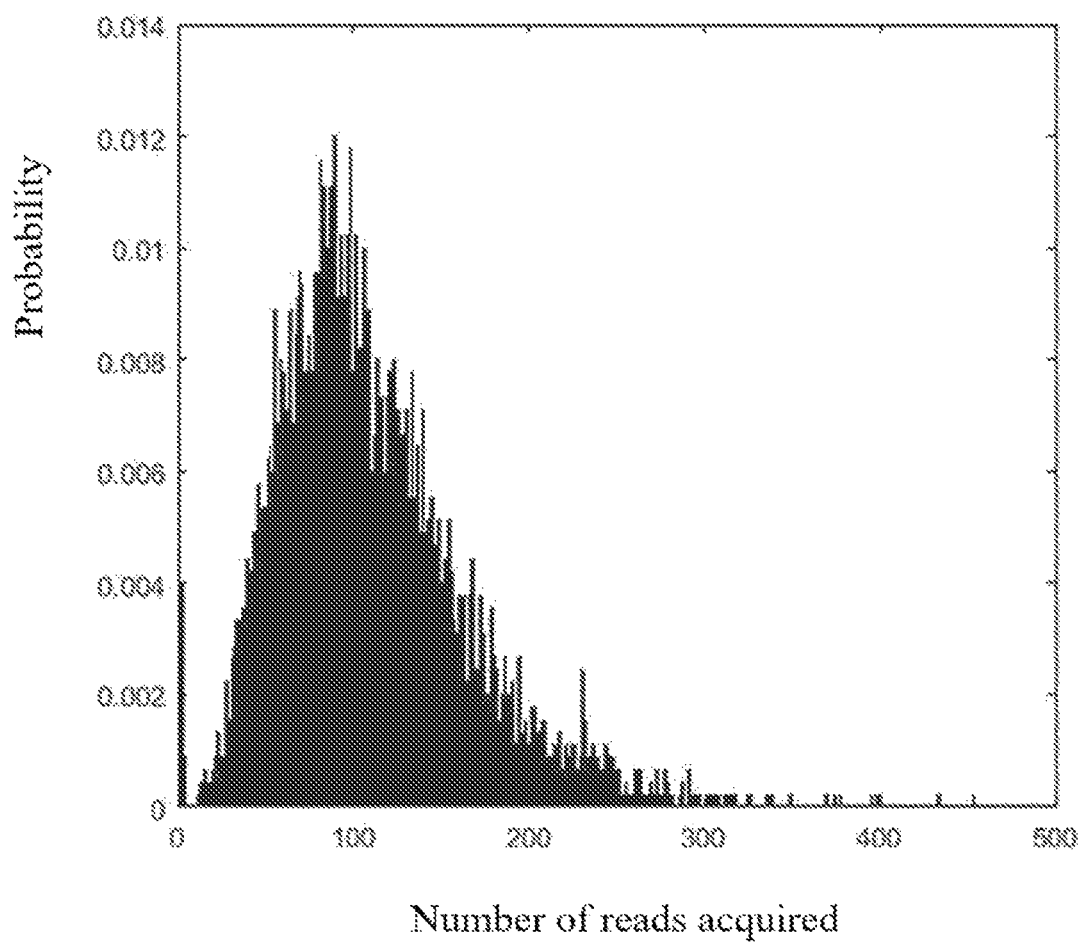
FIG. 12 is a probability histogram showing the numbers of NGS reads corresponding to individually designed DNA libraries.

FIG. 12 is a probability histogram showing the numbers of NGS reads corresponding to individually designed DNA libraries. Referring to FIG. 12, the X-axis represents the number of NGS reads corresponding to each DNA library design and the Y-axis represents the probability of the corresponding results. 0.5% (25) corresponding to 0 in the X-axis means that there are no NGS reads corresponding to 25 library designs. In response to this, designs having their own repeating data for error correction were used for recovery.

The NGS reads corresponding to each address were clustered and their representative results were acquired. By comparison with the repeating data in the other addresses, ~1% information errors and ~0.5% information losses were corrected and the existing data were recovered.

Figure 13A:
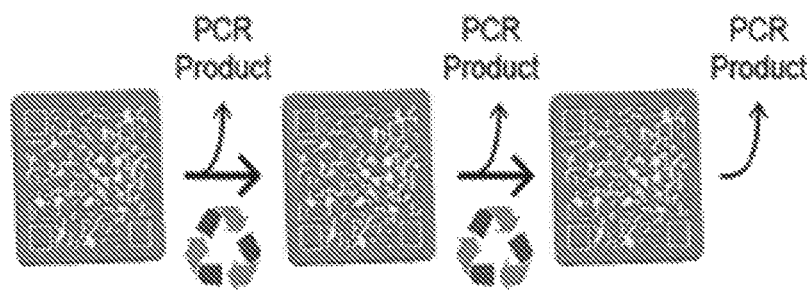
FIGS. 13(a) and (b) show test results for the ability of carrier particles bound with DNA molecules to preserve the DNA molecules with increasing reuse cycle of the carrier particles.
Figure 13B:
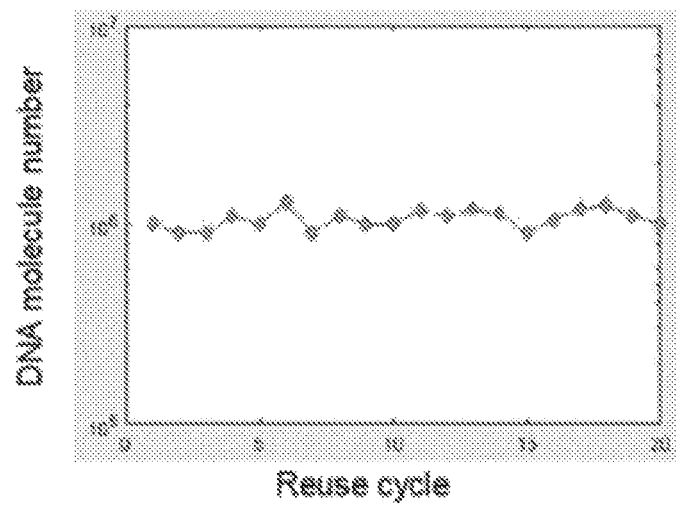

5. Test for Ability of the Biochemical Carriers to Preserve Biochemical Molecules when Reused The biochemical carriers were tested for their ability to preserve biochemical molecules when reused by the following procedure. FIG. 13 shows test results for the ability of the carrier particles bound with DNA molecules to preserve the DNA molecules with increasing reuse cycle of the carrier particles.

The carrier particles (sample 3) connected with DNA were amplified by PCR using a DNA polymerase, followed by washing several times. This procedure was repeated 20 times ((a) of FIG. 13).

As can be seen from the test results shown in (b) of FIG. 13, there were no changes in the amount of DNA on the carrier particles, which was confirmed by qPCR. That is, the amount of the original DNA was preserved even when the carrier particles were reused dozens of times.

The amplified DNA molecules were identified by next-generation sequencing (NGS). Perfect calls per million reads [pcpm] were plotted, and as a result, there was no change in overdispersion. These results are in contrast to previous results showing that there are changes in overdispersion during 20 times repeated amplification.

6. Storage and Selective Recovery of Data Sets

The ability of the carrier particles to preserve the original DNA enables storage of a plurality of various data sets in one particle and selective recovery of the data sets. For example, different primer sets can be used for selective recovery of data sets by PCR amplification. In this case, after different sets of biochemical molecules that can be recovered by different methods are stored in particles, a specific method can be applied to recover desired biochemical molecules.

A header file or summary file as well as the index code may be stored in the sequence of the biochemical molecules in the particles. In this case, the header file or summary file of the data can be checked before translation of the original file of the data. Thus, even when an accessible web page stored in the code is lost, the particles can function as a data center that has all data summaries.

Figure 14:
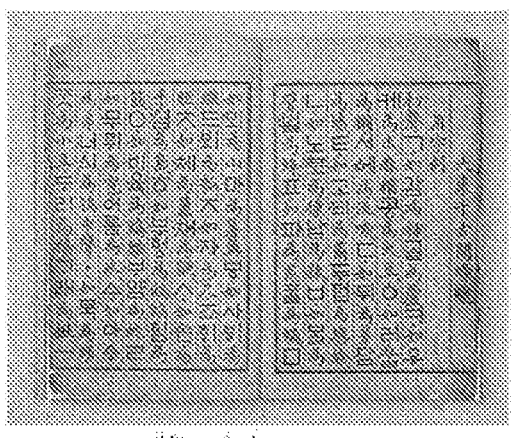
FIG. 14 shows three scanned image data files stored in biochemical carriers.
Figure 14:
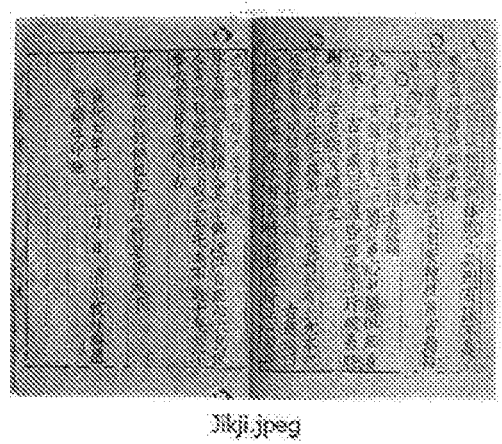
Figure 14:
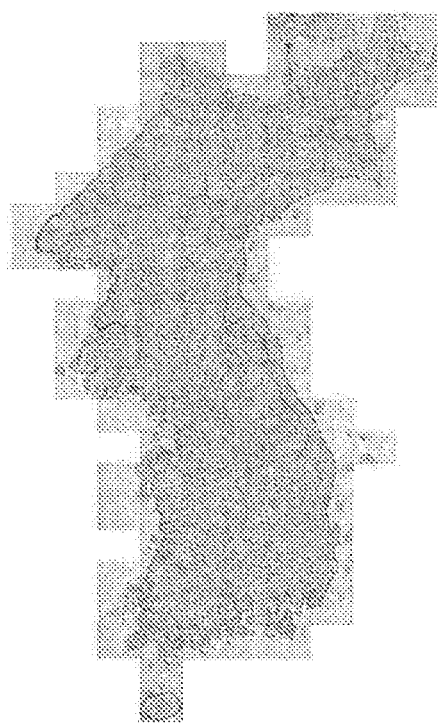

FIG. 14 shows three scanned image data files stored in biochemical carriers and FIG. 15 shows a portion taken from a description of the files shown in FIG. 14. Referring to FIGS. 14 and 15, each of the scanned files of Hunminjeongeum, Jikji, and Daedongyeojido (Hunmin.jpeg, Jikji.jpeg, and Daedongyeo.jpeg, respectively) as image data files was encoded into ~500 DNA sequences, each having a length of 150 nt, and their data description was stored in the particles. A QR code was used to acquire the data description from the particles. The DNA amplification and acquisition methods described in the code (see FIG. 15) were used to individually acquire the three image data files, if needed.

For example, when it is desired to acquire the Jikji.jpeg shown in FIG. 14, the recovery method is read from the description.txt shown in FIG. 15 and ATTTAGGTGACAC-TATAG/TGTGACCTGATCCGC is synthesized as a primer set corresponding to the Jikji-related DNA but different from primer sets corresponding to other image file-related DNA, DNA is amplified using the synthesized primer set, and the data can be restored by NGS. In addition, a Reed-Solomon (RS) code as an algorithm for correcting lost or erroneous data can be used to correct data errors.

According to the present disclosure, the biochemical substance as an original form can be retained even after amplification using a polymerase because the original form is connectively immobilized on the particles. Although the biochemical substance is adherent to the particles, no influence is given to the function of the biochemical substance to store information because the distal ends of the biochemical substance connected to the carrier particles are not directly involved in amplification. In addition, according to the present disclosure, the amount of the original biochemical molecules can be preserved without loss even when the biochemical carriers are reused dozens of times. As a result, the present disclosure can first establish a write-once-read-many (WORM) system as a methodology for storing data in a biochemical substance.

Although the present disclosure has been described herein with reference to the foregoing embodiments, those skilled in the art will appreciate that various modifications can be made to the embodiments, without departing from the spirit and scope of the present disclosure.

What is claimed is:

1. A biochemical carrier comprising: biochemical molecules having a sequence into which digital data information is encoded; a carrier particle composed of a polymer matrix and in which the biochemical molecules are connected to the surface or inside of the polymer matrix; and an index code introduced into the carrier particle.

2. The biochemical carrier according to claim 1, wherein the polymer matrix is composed of a photocurable polymer.

3. The biochemical carrier according to claim 1, wherein the polymer matrix is porous.

4. The biochemical carrier according to claim 1, wherein the biochemical molecules have functional groups that are chemically connected to the chains of the polymer matrix.

5. The biochemical carrier according to claim 1, further comprising a protective layer surrounding the surface of the carrier particle.

6. The biochemical carrier according to claim 5, wherein the protective layer is formed using a metal or metal oxide.

7. The biochemical carrier according to claim 5, wherein the protective layer is a silica shell that is connected to the surface of the carrier particle via —Si—O—Si— bonds.

8. The biochemical carrier according to claim 1, wherein the carrier particle has a volume of $10^{-9}$ to 1 mm$^3$.

9. The biochemical carrier according to claim 1, wherein the index code contains information about the biochemical molecules connected to the carrier particle, a method for reacquiring and analyzing the biochemical molecules to decode encoded digital information or a method for accessing to the decoding method.

10. The biochemical carrier according to claim 1, wherein the index code is selected from the group consisting of QR codes, binary codes, graphical codes, spectral codes, and topographical codes.

11. A method for fabricating biochemical carriers, comprising: encoding digital data into a sequence of biochemical molecules; synthesizing the biochemical molecules based on the encoded sequence; mixing the biochemical molecules with a photocurable material; curing the mixture to obtain carrier particles comprising a polymer matrix; and introducing an index code into the carrier particles simultaneously with or separately from the curing.

12. The method according to claim 11, further comprising forming protective layers surrounding the carrier particles.

13. The method according to claim 11, wherein the biochemical molecules have functional groups that are chemically connected to the chains of the polymer matrix.

14. The method according to claim 11, wherein the mixture further comprises a porogen.

15. The method according to claim 14, wherein the porogen is a polyalkylene glycol.

16. The method according to claim 11, wherein the carrier particles are obtained by optofluidic maskless lithography.

17. A method for restoring digital data from a biochemical carrier comprising:
- analyzing the index code of the biochemical carrier; wherein
- the biochemical carrier comprises:
  - biochemical molecules having a sequence into which digital data information is encoded;
  - a carrier particle composed of a polymer matrix and in which the biochemical molecules are connected to the surface or inside of the polymer matrix; and
  - an index code introduced into the carrier particle,
- reacquiring the biochemical molecules from the biochemical carrier based on the analytical results of the index code;
- sequencing the biochemical molecules; and
- decoding the sequencing results to restore digital data.

18. The method according to claim 17, wherein the carrier particles stores a plurality of data sets and a desired data set is selectively restored from the plurality of data sets.

* * * * *

SEQUENCE LISTING

<160> NUMBER OF SEQ ID NOS: 166

<210> SEQ ID NO 1
<211> LENGTH: 143

<212> TYPE: DNA
<213> ORGANISM: Artificial Sequence
<220> FEATURE:
<223> OTHER INFORMATION: Synthesized

<400> SEQUENCE: 1
tccctacacg acgctcttcc gatctccaac aacaacagta gtaactttca gctgcagtcc    60
ttgaacacct catatcttcc cagtctgaga ctctcgatca tcatctgtat acagactaag   120
atcggaagag cacacgtctg aac                                           143

<210> SEQ ID NO 2
<211> LENGTH: 143
<212> TYPE: DNA
<213> ORGANISM: Artificial Sequence
<220> FEATURE:
<223> OTHER INFORMATION: Synthesized

<400> SEQUENCE: 2
tccctacacg acgctcttcc gatcttcaac aacaacacat actactagtt gcagcagctg    60
agattctaga tcagtcagtt tcagagacaa cagcacagtc aacgactacg ataaggacag   120
atcggaagag cacacgtctg aac                                           143

<210> SEQ ID NO 3
<211> LENGTH: 143
<212> TYPE: DNA
<213> ORGANISM: Artificial Sequence
<220> FEATURE:
<223> OTHER INFORMATION: Synthesized

<400> SEQUENCE: 3
tccctacacg acgctcttcc gatctgcaac aacaacaact tcaaactcat caccatgagt    60
atgatgccat gatagtcgac catgtacact aacagctagt catccagtca gcactagaag   120
atcggaagag cacacgtctg aac                                           143

<210> SEQ ID NO 4
<211> LENGTH: 143
<212> TYPE: DNA
<213> ORGANISM: Artificial Sequence
<220> FEATURE:
<223> OTHER INFORMATION: Synthesized

<400> SEQUENCE: 4
tccctacacg acgctcttcc gatctctaac aacaacaagc acacgtagcg tatgagacgg    60
agtaatctgt tcacgatgag tactacatat ctaccaccat tgatgaccta gagctcacag   120
atcggaagag cacacgtctg aac                                           143

<210> SEQ ID NO 5
<211> LENGTH: 143
<212> TYPE: DNA
<213> ORGANISM: Artificial Sequence
<220> FEATURE:
<223> OTHER INFORMATION: Synthesized

<400> SEQUENCE: 5
tccctacacg acgctcttcc gatctgtaac aacaacaagt gactgcgtag gagctcgact    60
actaatcgca ccaccatacg atgatagatt cggacgaaac ggtactacta agacaatcag   120
atcggaagag cacacgtctg aac                                           143

<210> SEQ ID NO 6

```
<211> LENGTH: 143
<212> TYPE: DNA
<213> ORGANISM: Artificial Sequence
<220> FEATURE:
<223> OTHER INFORMATION: Synthesized

<400> SEQUENCE: 6
tccctacacg acgctcttcc gatctagaac aacaacacac gtccatggag ctggagattg    60
aagcgtcgta tgagtaagaa gactagataa ccctccagtc aacagctgtc gtgcaccaag   120
atcggaagag cacacgtctg aac                                           143

<210> SEQ ID NO 7
<211> LENGTH: 143
<212> TYPE: DNA
<213> ORGANISM: Artificial Sequence
<220> FEATURE:
<223> OTHER INFORMATION: Synthesized

<400> SEQUENCE: 7
tccctacacg acgctcttcc gatctcgaac aacaacagga agcccagcta cactactaca    60
taacttctac gacaacttca gccattcaca tcgactaaca ctaagtgctt gcctaactag   120
atcggaagag cacacgtctg aac                                           143

<210> SEQ ID NO 8
<211> LENGTH: 143
<212> TYPE: DNA
<213> ORGANISM: Artificial Sequence
<220> FEATURE:
<223> OTHER INFORMATION: Synthesized

<400> SEQUENCE: 8
tccctacacg acgctcttcc gatcttgaac aacaacagac agacatccac attcacattc    60
agacagatgt gcactacata gttctccatg atgacgtgat atccaccgtc gacaggtaag   120
atcggaagag cacacgtctg aac                                           143

<210> SEQ ID NO 9
<211> LENGTH: 143
<212> TYPE: DNA
<213> ORGANISM: Artificial Sequence
<220> FEATURE:
<223> OTHER INFORMATION: Synthesized

<400> SEQUENCE: 9
tccctacacg acgctcttcc gatctggaac aacaacagta acagtacata gtgtcagcag    60
ctgaacacta catatcagcc gtggaaacga ctctgcatga ttcggagctc tcctccagag   120
atcggaagag cacacgtctg aac                                           143

<210> SEQ ID NO 10
<211> LENGTH: 143
<212> TYPE: DNA
<213> ORGANISM: Artificial Sequence
<220> FEATURE:
<223> OTHER INFORMATION: Synthesized

<400> SEQUENCE: 10
tccctacacg acgctcttcc gatctaacac aacaacacat tcttcaaagt caagtgtagg    60
agatctatgc tcagattgca actgagtccc agcattcgat aacgactacg tacagtctag   120
atcggaagag cacacgtctg aac                                           143
```

```
<210> SEQ ID NO 11
<211> LENGTH: 143
<212> TYPE: DNA
<213> ORGANISM: Artificial Sequence
<220> FEATURE:
<223> OTHER INFORMATION: Synthesized

<400> SEQUENCE: 11
tccctacacg acgctcttcc gatctcacac aacaacaact tcaagtgtca acgactgagt      60
aggacatatc ttctcagatg acgtaacaca tacagactca gcagtagata gccgtccaag     120
atcggaagag cacacgtctg aac                                             143

<210> SEQ ID NO 12
<211> LENGTH: 143
<212> TYPE: DNA
<213> ORGANISM: Artificial Sequence
<220> FEATURE:
<223> OTHER INFORMATION: Synthesized

<400> SEQUENCE: 12
tccctacacg acgctcttcc gatcttacac aacaacaagc acacactcaa tctgagacag      60
aacatgatac agtcgagacc taaaccatat ctcagctcga tgacatccta ctcagcacag     120
atcggaagag cacacgtctg aac                                             143

<210> SEQ ID NO 13
<211> LENGTH: 143
<212> TYPE: DNA
<213> ORGANISM: Artificial Sequence
<220> FEATURE:
<223> OTHER INFORMATION: Synthesized

<400> SEQUENCE: 13
tccctacacg acgctcttcc gatctgacac aacaacaagt gtcggagtaa acgataacca      60
tagttctgtc cattgatctc ctgtaatctt caaccattga gacactacta agactcatag     120
atcggaagag cacacgtctg aac                                             143

<210> SEQ ID NO 14
<211> LENGTH: 143
<212> TYPE: DNA
<213> ORGANISM: Artificial Sequence
<220> FEATURE:
<223> OTHER INFORMATION: Synthesized

<400> SEQUENCE: 14
tccctacacg acgctcttcc gatctatcac aacaacacac tcagactgag atcgactaaa      60
ctcacacttc tgagtattca gatgatcatc ttgaccagac aacagccata gtagcggtag     120
atcggaagag cacacgtctg aac                                             143

<210> SEQ ID NO 15
<211> LENGTH: 143
<212> TYPE: DNA
<213> ORGANISM: Artificial Sequence
<220> FEATURE:
<223> OTHER INFORMATION: Synthesized

<400> SEQUENCE: 15
tccctacacg acgctcttcc gatctctcac aacaacagga atcgtagtca gagtaagctc      60
aagcgtacga gacccagcac atgataacga catcgtaaac ctaagtagtt gcgactcaag     120
atcggaagag cacacgtctg aac                                             143
```

<210> SEQ ID NO 16
<211> LENGTH: 143
<212> TYPE: DNA
<213> ORGANISM: Artificial Sequence
<220> FEATURE:
<223> OTHER INFORMATION: Synthesized

<400> SEQUENCE: 16
tccctacacg acgctcttcc gatctttcac aacaacagac tgacattcac attgatgcaa    60
caactacaca acacatctat gttcacatcc agatggacta atccaccacg gacctttcag   120
atcggaagag cacacgtctg aac                                            143

<210> SEQ ID NO 17
<211> LENGTH: 143
<212> TYPE: DNA
<213> ORGANISM: Artificial Sequence
<220> FEATURE:
<223> OTHER INFORMATION: Synthesized

<400> SEQUENCE: 17
tccctacacg acgctcttcc gatctgtcac aacaacacca ctaactctac tacatagtag    60
catcgtccta catagatacg caccatgagg acctgtaaga ttcggactat acactctcag   120
atcggaagag cacacgtctg aac                                            143

<210> SEQ ID NO 18
<211> LENGTH: 143
<212> TYPE: DNA
<213> ORGANISM: Artificial Sequence
<220> FEATURE:
<223> OTHER INFORMATION: Synthesized

<400> SEQUENCE: 18
tccctacacg acgctcttcc gatctagcac aacaacacat ttcagctcag tctctatctg    60
agatcctgat agagatggag tatgaggtgt aagaagattc aacgacgacg tccagactag   120
atcggaagag cacacgtctg aac                                            143

<210> SEQ ID NO 19
<211> LENGTH: 143
<212> TYPE: DNA
<213> ORGANISM: Artificial Sequence
<220> FEATURE:
<223> OTHER INFORMATION: Synthesized

<400> SEQUENCE: 19
tccctacacg acgctcttcc gatcttgcac aacaacagta agaagtgata acggaccaga    60
tcctactcta gattcaacat acggtaaccg aagttcaaac catccatgtc cttgaagtag   120
atcggaagag cacacgtctg aac                                            143

<210> SEQ ID NO 20
<211> LENGTH: 143
<212> TYPE: DNA
<213> ORGANISM: Artificial Sequence
<220> FEATURE:
<223> OTHER INFORMATION: Synthesized

<400> SEQUENCE: 20
tccctacacg acgctcttcc gatctcatac aacaacagta taccactcaa gctgagtaca    60
ctcatgtcat tcacgaagat gtgcactaaa cagtaaccga tgacatagaa gccacggaag   120
atcggaagag cacacgtctg aac                                            143

<210> SEQ ID NO 21
<211> LENGTH: 143
<212> TYPE: DNA
<213> ORGANISM: Artificial Sequence
<220> FEATURE:
<223> OTHER INFORMATION: Synthesized

<400> SEQUENCE: 21
tccctacacg acgctcttcc gatctgatac aacaacatga tgtggagtag gagatgcact    60
aacaaagtct ccatgactac tagatatccg tcaccgatga gacgtattca caagcctcag   120
atcggaagag cacacgtctg aac                                           143

<210> SEQ ID NO 22
<211> LENGTH: 143
<212> TYPE: DNA
<213> ORGANISM: Artificial Sequence
<220> FEATURE:
<223> OTHER INFORMATION: Synthesized

<400> SEQUENCE: 22
tccctacacg acgctcttcc gatctactac aacaacacgt tgcgacccag gtggactaaa    60
ctaccacgga aacgtacgtt gctgattcgt catctgagac ccactacata acctacagag   120
atcggaagag cacacgtctg aac                                           143

<210> SEQ ID NO 23
<211> LENGTH: 143
<212> TYPE: DNA
<213> ORGANISM: Artificial Sequence
<220> FEATURE:
<223> OTHER INFORMATION: Synthesized

<400> SEQUENCE: 23
tccctacacg acgctcttcc gatctcctac aacaacacgt ccagtagtag cagtaaagca    60
tgtcgtaaac gtcaactgca tcgtcaacac agtagacgca cattgagtcg catgttctag   120
atcggaagag cacacgtctg aac                                           143

<210> SEQ ID NO 24
<211> LENGTH: 143
<212> TYPE: DNA
<213> ORGANISM: Artificial Sequence
<220> FEATURE:
<223> OTHER INFORMATION: Synthesized

<400> SEQUENCE: 24
tccctacacg acgctcttcc gatcttctac aacaacacat taccatgcac tactacatag    60
cgtcgacgtc acactacatt acagtgcaag agctaaccat atctctgcac caaaccgtag   120
atcggaagag cacacgtctg aac                                           143

<210> SEQ ID NO 25
<211> LENGTH: 143
<212> TYPE: DNA
<213> ORGANISM: Artificial Sequence
<220> FEATURE:
<223> OTHER INFORMATION: Synthesized

<400> SEQUENCE: 25
tccctacacg acgctcttcc gatctgctac aacaacatac ggtactctat gatgcagctg    60
cctatgtaca catagatacg tcccatgatg agatctaatc ttccacccag acctaggaag   120
atcggaagag cacacgtctg aac                                              143

<210> SEQ ID NO 26
<211> LENGTH: 143
<212> TYPE: DNA
<213> ORGANISM: Artificial Sequence
<220> FEATURE:
<223> OTHER INFORMATION: Synthesized

<400> SEQUENCE: 26
tccctacacg acgctcttcc gatctagtac aacaacagat ggacgaaaca tcgtccagcc       60
atgtcgacac cagggatgac agatctgacg tctcgcatac gtcaactgag tcggacagag      120
atcggaagag cacacgtctg aac                                              143

<210> SEQ ID NO 27
<211> LENGTH: 143
<212> TYPE: DNA
<213> ORGANISM: Artificial Sequence
<220> FEATURE:
<223> OTHER INFORMATION: Synthesized

<400> SEQUENCE: 27
tccctacacg acgctcttcc gatctcgtac aacaacacca cattctgatc agccacctca       60
gacatgacct cctaagtgac agggtagctc agatggagta ctcaagtacc cagtccagag      120
atcggaagag cacacgtctg aac                                              143

<210> SEQ ID NO 28
<211> LENGTH: 143
<212> TYPE: DNA
<213> ORGANISM: Artificial Sequence
<220> FEATURE:
<223> OTHER INFORMATION: Synthesized

<400> SEQUENCE: 28
tccctacacg acgctcttcc gatcttgtac aacaacattc cgagtatgtg ataagggtgg       60
agtagcacca tcacgagacg caaagtgaaa gccatctctc ccatcacaca tcagccctag      120
atcggaagag cacacgtctg aac                                              143

<210> SEQ ID NO 29
<211> LENGTH: 143
<212> TYPE: DNA
<213> ORGANISM: Artificial Sequence
<220> FEATURE:
<223> OTHER INFORMATION: Synthesized

<400> SEQUENCE: 29
tccctacacg acgctcttcc gatctggtac aacaacaagt gatgacactc agatcggaca       60
gagctgctca ctcctaaagc gatgcagacg tcacgcacag atcccttaca gtcgaatcag      120
atcggaagag cacacgtctg aac                                              143

<210> SEQ ID NO 30
<211> LENGTH: 143
<212> TYPE: DNA
<213> ORGANISM: Artificial Sequence
<220> FEATURE:
<223> OTHER INFORMATION: Synthesized

<400> SEQUENCE: 30
tccctacacg acgctcttcc gatctaagac aacaacaagt aaggtccctg acgcaggaac       60
aatcgactca cgaaagttcc gtcacgctga cgtctgccag gcacatgacc gtacacacag      120

```
atcggaagag cacacgtctg aac                                              143

<210> SEQ ID NO 31
<211> LENGTH: 143
<212> TYPE: DNA
<213> ORGANISM: Artificial Sequence
<220> FEATURE:
<223> OTHER INFORMATION: Synthesized

<400> SEQUENCE: 31
tccctacacg acgctcttcc gatctcagac aacaacaaag atcactagtg atcgtagaga      60
tagccaggac gtcggtcagc atcgaccttg tctatgaaca aactactctt gatacatcag    120
atcggaagag cacacgtctg aac                                              143

<210> SEQ ID NO 32
<211> LENGTH: 143
<212> TYPE: DNA
<213> ORGANISM: Artificial Sequence
<220> FEATURE:
<223> OTHER INFORMATION: Synthesized

<400> SEQUENCE: 32
tccctacacg acgctcttcc gatctacacc aacaacagtc catcgtgtag tcggaacata      60
cgtcagccct agctgacgtt tcctagactt cctaagcgct tgcgtactag atcatggtag    120
atcggaagag cacacgtctg aac                                              143

<210> SEQ ID NO 33
<211> LENGTH: 143
<212> TYPE: DNA
<213> ORGANISM: Artificial Sequence
<220> FEATURE:
<223> OTHER INFORMATION: Synthesized

<400> SEQUENCE: 33
tccctacacg acgctcttcc gatctccacc aacaacagct actcagtgac gtacatacgt      60
aagtcgaaca tgtgcaatca tcccagcttc aactgctgca gcagtaccac ctggtgacag    120
atcggaagag cacacgtctg aac                                              143

<210> SEQ ID NO 34
<211> LENGTH: 143
<212> TYPE: DNA
<213> ORGANISM: Artificial Sequence
<220> FEATURE:
<223> OTHER INFORMATION: Synthesized

<400> SEQUENCE: 34
tccctacacg acgctcttcc gatcttcacc aacaacaact tgactcacta gctgactatc      60
tactagcagt cgtggatacg gacgaagact acgtcacgta tacttcggta ctgcagtcag    120
atcggaagag cacacgtctg aac                                              143

<210> SEQ ID NO 35
<211> LENGTH: 143
<212> TYPE: DNA
<213> ORGANISM: Artificial Sequence
<220> FEATURE:
<223> OTHER INFORMATION: Synthesized

<400> SEQUENCE: 35
tccctacacg acgctcttcc gatctgcacc aacaacaaag cgtggttgct acgatttctc      60
```

```
aagacgtgca catgacttcc atactagccg tcgtctcatc gatttcagat gaaaggtaag      120
atcggaagag cacacgtctg aac                                              143

<210> SEQ ID NO 36
<211> LENGTH: 143
<212> TYPE: DNA
<213> ORGANISM: Artificial Sequence
<220> FEATURE:
<223> OTHER INFORMATION: Synthesized

<400> SEQUENCE: 36
tccctacacg acgctcttcc gatctctacc aacaacatga gctggaaagg atttcagaac      60
agcttgcgta ctatctttca cttgttctcg tagcgacgga agcagaaacg ctcctatcag     120
atcggaagag cacacgtctg aac                                              143

<210> SEQ ID NO 37
<211> LENGTH: 143
<212> TYPE: DNA
<213> ORGANISM: Artificial Sequence
<220> FEATURE:
<223> OTHER INFORMATION: Synthesized

<400> SEQUENCE: 37
tccctacacg acgctcttcc gatctgtacc aacaacatca tactctctat tcccttctcg      60
tcacccaatc ccattcagat gtgcttgcta ctacggaagc tcatcacgtc acatccatag     120
atcggaagag cacacgtctg aac                                              143

<210> SEQ ID NO 38
<211> LENGTH: 143
<212> TYPE: DNA
<213> ORGANISM: Artificial Sequence
<220> FEATURE:
<223> OTHER INFORMATION: Synthesized

<400> SEQUENCE: 38
tccctacacg acgctcttcc gatctagacc aacaacacta ctacgaactc ctagatctcg      60
tctaatctga gtagcaaacg gtggagtata cgatcatact acacgttgca gcttctgcag     120
atcggaagag cacacgtctg aac                                              143

<210> SEQ ID NO 39
<211> LENGTH: 143
<212> TYPE: DNA
<213> ORGANISM: Artificial Sequence
<220> FEATURE:
<223> OTHER INFORMATION: Synthesized

<400> SEQUENCE: 39
tccctacacg acgctcttcc gatctcgacc aacaacatac ccacgttcat gaggtcacag      60
actagacttc acttcagctg caacaatcgt cttcacttga gcttgcggag accctcctag     120
atcggaagag cacacgtctg aac                                              143

<210> SEQ ID NO 40
<211> LENGTH: 143
<212> TYPE: DNA
<213> ORGANISM: Artificial Sequence
<220> FEATURE:
<223> OTHER INFORMATION: Synthesized

<400> SEQUENCE: 40
tccctacacg acgctcttcc gatcttgacc aacaacagta gtacacacat gaccaagcct      60
```

```
accaagtaga agcatcgcag taatctacag cagctgatga tgcctaatct cttgaccaag    120
atcggaagag cacacgtctg aac                                            143

<210> SEQ ID NO 41
<211> LENGTH: 143
<212> TYPE: DNA
<213> ORGANISM: Artificial Sequence
<220> FEATURE:
<223> OTHER INFORMATION: Synthesized

<400> SEQUENCE: 41
tccctacacg acgctcttcc gatctggacc aacaacaagc actcaccgtt caacataccc    60
agtccgatca cgtccaggat acgacttccc tctacgtgca ctcctagtct tccctccaag    120
atcggaagag cacacgtctg aac                                            143

<210> SEQ ID NO 42
<211> LENGTH: 143
<212> TYPE: DNA
<213> ORGANISM: Artificial Sequence
<220> FEATURE:
<223> OTHER INFORMATION: Synthesized

<400> SEQUENCE: 42
tccctacacg acgctcttcc gatctaaccc aacaacaact aaggacgcag acggaggtgt    60
acgaagccgt ggaactatct tccctagaag acacgctact atcccacatc tacacgcaag    120
atcggaagag cacacgtctg aac                                            143

<210> SEQ ID NO 43
<211> LENGTH: 143
<212> TYPE: DNA
<213> ORGANISM: Artificial Sequence
<220> FEATURE:
<223> OTHER INFORMATION: Synthesized

<400> SEQUENCE: 43
tccctacacg acgctcttcc gatctcaccc aacaacatga tgtggaggat acgtcagcac    60
tagctgatgc acaagagtct tccctagcgg tgtcacatac tgaacttcaa ctcaggcaag    120
atcggaagag cacacgtctg aac                                            143

<210> SEQ ID NO 44
<211> LENGTH: 143
<212> TYPE: DNA
<213> ORGANISM: Artificial Sequence
<220> FEATURE:
<223> OTHER INFORMATION: Synthesized

<400> SEQUENCE: 44
tccctacacg acgctcttcc gatcttaccc aacaacacgt tgctacatcg tattcagcaa    60
gtgagcacta ggactacata gaaacggtcc aacagacgat ttcactacac gttcagctag    120
atcggaagag cacacgtctg aac                                            143

<210> SEQ ID NO 45
<211> LENGTH: 143
<212> TYPE: DNA
<213> ORGANISM: Artificial Sequence
<220> FEATURE:
<223> OTHER INFORMATION: Synthesized

<400> SEQUENCE: 45
```
tccctacacg acgctcttcc gatctgaccc aacaacacgt gtactattct ctactacatg    60
ttcagcacta ggacctacta gctgtccaac atgagtagct agatcacgtc gtggttctag   120
atcggaagag cacacgtctg aac                                            143

<210> SEQ ID NO 46
<211> LENGTH: 143
<212> TYPE: DNA
<213> ORGANISM: Artificial Sequence
<220> FEATURE:
<223> OTHER INFORMATION: Synthesized

<400> SEQUENCE: 46
tccctacacg acgctcttcc gatctatccc aacaacaatc tacgcacctt catgttgttg    60
caactaccca agctcaaagc gttgcacaga cgtcgctcga agctgtcgta gcctatacag   120
atcggaagag cacacgtctg aac                                            143

<210> SEQ ID NO 47
<211> LENGTH: 143
<212> TYPE: DNA
<213> ORGANISM: Artificial Sequence
<220> FEATURE:
<223> OTHER INFORMATION: Synthesized

<400> SEQUENCE: 47
tccctacacg acgctcttcc gatctctccc aacaacatac gtaggatcaa cagctcgtgt    60
agacgtatgc actacacgtg tcgcatacga tttcagcagc ggttgcagat acgtagtaag   120
atcggaagag cacacgtctg aac                                            143

<210> SEQ ID NO 48
<211> LENGTH: 143
<212> TYPE: DNA
<213> ORGANISM: Artificial Sequence
<220> FEATURE:
<223> OTHER INFORMATION: Synthesized

<400> SEQUENCE: 48
tccctacacg acgctcttcc gatctttccc aacaacatgt cctggtacac gtccagcata    60
cggtgctact aagttcgtca catacgtatt cactacatga gcacacctag atatcgacag   120
atcggaagag cacacgtctg aac                                            143

<210> SEQ ID NO 49
<211> LENGTH: 143
<212> TYPE: DNA
<213> ORGANISM: Artificial Sequence
<220> FEATURE:
<223> OTHER INFORMATION: Synthesized

<400> SEQUENCE: 49
tccctacacg acgctcttcc gatctgtccc aacaacattc gcaggttgac gttcatacct    60
agctcgaaac cgtggaacaa gacatgctcc taactctgca tgcatcccat tccatcgtag   120
atcggaagag cacacgtctg aac                                            143

<210> SEQ ID NO 50
<211> LENGTH: 143
<212> TYPE: DNA
<213> ORGANISM: Artificial Sequence
<220> FEATURE:
<223> OTHER INFORMATION: Synthesized

<400> SEQUENCE: 50

```
tccctacacg acgctcttcc gatctagccc aacaacacga catgatagca gagtagtatt    60
cacttgacgt tgcacaatcc tattcagcac agctcgtcca ctatactcta ctagacacag   120
atcggaagag cacacgtctg aac                                           143

<210> SEQ ID NO 51
<211> LENGTH: 143
<212> TYPE: DNA
<213> ORGANISM: Artificial Sequence
<220> FEATURE:
<223> OTHER INFORMATION: Synthesized

<400> SEQUENCE: 51
tccctacacg acgctcttcc gatcttgccc aacaacaagc tgaagacatc tactaactcg    60
aaaccgtcgt cgaatcggtt gtagaacatg agcactctac ccattccgat gtcatagcag   120
atcggaagag cacacgtctg aac                                           143

<210> SEQ ID NO 52
<211> LENGTH: 143
<212> TYPE: DNA
<213> ORGANISM: Artificial Sequence
<220> FEATURE:
<223> OTHER INFORMATION: Synthesized

<400> SEQUENCE: 52
tccctacacg acgctcttcc gatctcatcc aacaacagct gtacatgacc cattcagaac    60
acgtcgttac gtagacttcg catgaggtgc actcgacgtc agtcgactat gattccgaag   120
atcggaagag cacacgtctg aac                                           143

<210> SEQ ID NO 53
<211> LENGTH: 143
<212> TYPE: DNA
<213> ORGANISM: Artificial Sequence
<220> FEATURE:
<223> OTHER INFORMATION: Synthesized

<400> SEQUENCE: 53
tccctacacg acgctcttcc gatctgatcc aacaacacac cattgtccaa gtagaaactg    60
tcgtcgagac gatagccctt acgctgcagg agacgctcgt agatgagctg caagtaagag   120
atcggaagag cacacgtctg aac                                           143

<210> SEQ ID NO 54
<211> LENGTH: 143
<212> TYPE: DNA
<213> ORGANISM: Artificial Sequence
<220> FEATURE:
<223> OTHER INFORMATION: Synthesized

<400> SEQUENCE: 54
tccctacacg acgctcttcc gatctactcc aacaacactc ggtagtagca gaagctgatg    60
catcatcggt catactagag accactgaga cgctgctaga agcagtggag caatcgtaag   120
atcggaagag cacacgtctg aac                                           143

<210> SEQ ID NO 55
<211> LENGTH: 143
<212> TYPE: DNA
<213> ORGANISM: Artificial Sequence
<220> FEATURE:
<223> OTHER INFORMATION: Synthesized
```

<400> SEQUENCE: 55
tccctacacg acgctcttcc gatctcctcc aacaacagac atcgatagct tctgtgcact      60
cctaggatgc agaagatgac catgctactc ttgcacttca cgtgcagact acgaccatag     120
atcggaagag cacacgtctg aac                                             143

<210> SEQ ID NO 56
<211> LENGTH: 143
<212> TYPE: DNA
<213> ORGANISM: Artificial Sequence
<220> FEATURE:
<223> OTHER INFORMATION: Synthesized

<400> SEQUENCE: 56
tccctacacg acgctcttcc gatcttctcc aacaacagga agtcagacag ctgctgacta      60
cccattcact aagcgtgcaa tctaccattt ccctagccgt cacgtagacg tatgactaag     120
atcggaagag cacacgtctg aac                                             143

<210> SEQ ID NO 57
<211> LENGTH: 143
<212> TYPE: DNA
<213> ORGANISM: Artificial Sequence
<220> FEATURE:
<223> OTHER INFORMATION: Synthesized

<400> SEQUENCE: 57
tccctacacg acgctcttcc gatctgctcc aacaacagtc catcgttgac atagtcactc      60
agtatgtgct agttgcagtg gtagcctaga cgatggtcag cctgctcacg gtgtagatag     120
atcggaagag cacacgtctg aac                                             143

<210> SEQ ID NO 58
<211> LENGTH: 143
<212> TYPE: DNA
<213> ORGANISM: Artificial Sequence
<220> FEATURE:
<223> OTHER INFORMATION: Synthesized

<400> SEQUENCE: 58
tccctacacg acgctcttcc gatctagtcc aacaacaagc tgtgacgcag atttccactc      60
agcatcaagc cctcactacc atatctgcct cggtagatac ctacattcta cagctagtag     120
atcggaagag cacacgtctg aac                                             143

<210> SEQ ID NO 59
<211> LENGTH: 143
<212> TYPE: DNA
<213> ORGANISM: Artificial Sequence
<220> FEATURE:
<223> OTHER INFORMATION: Synthesized

<400> SEQUENCE: 59
tccctacacg acgctcttcc gatctcgtcc aacaacatca ctcaagcata agctcggttg      60
ccgtaacgca gctcactgac agggactcaa cagtatcttc acatcaagat accgacgtag     120
atcggaagag cacacgtctg aac                                             143

<210> SEQ ID NO 60
<211> LENGTH: 143
<212> TYPE: DNA
<213> ORGANISM: Artificial Sequence
<220> FEATURE:
<223> OTHER INFORMATION: Synthesized

```
<400> SEQUENCE: 60
tccctacacg acgctcttcc gatcttgtcc aacaacagga gtaagcctcg gtgactgatg    60
cgacgtaaca tgtgacgact acgtcgatcc aatctaccac ttccataagc acagtcacag   120
atcggaagag cacacgtctg aac                                           143

<210> SEQ ID NO 61
<211> LENGTH: 143
<212> TYPE: DNA
<213> ORGANISM: Artificial Sequence
<220> FEATURE:
<223> OTHER INFORMATION: Synthesized

<400> SEQUENCE: 61
tccctacacg acgctcttcc gatctggtcc aacaacattc ggtgtcagat tctgcaagag    60
cctctaccct acaccacatc caccatgatg acctcgatca aacgtagtcc agagttgcag   120
atcggaagag cacacgtctg aac                                           143

<210> SEQ ID NO 62
<211> LENGTH: 143
<212> TYPE: DNA
<213> ORGANISM: Artificial Sequence
<220> FEATURE:
<223> OTHER INFORMATION: Synthesized

<400> SEQUENCE: 62
tccctacacg acgctcttcc gatctaagcc aacaacaagc tgaaacgcaa cttcagtcag    60
tgtcggtgta ccttcaaaga agtacagaga cagcgatagc ggtcgtctct gactaacaag   120
atcggaagag cacacgtctg aac                                           143

<210> SEQ ID NO 63
<211> LENGTH: 143
<212> TYPE: DNA
<213> ORGANISM: Artificial Sequence
<220> FEATURE:
<223> OTHER INFORMATION: Synthesized

<400> SEQUENCE: 63
tccctacacg acgctcttcc gatctcagcc aacaacagct agaacacgtt gccattactt    60
cgcacgaaga tgacactgcg acccaagcag aagaagtcca tacatcccaa gtgtaaagag   120
atcggaagag cacacgtctg aac                                           143

<210> SEQ ID NO 64
<211> LENGTH: 143
<212> TYPE: DNA
<213> ORGANISM: Artificial Sequence
<220> FEATURE:
<223> OTHER INFORMATION: Synthesized

<400> SEQUENCE: 64
tccctacacg acgctcttcc gatctacatc aacaacacga agctctgcag atgtagtatt    60
ccctctaagt gcagtaagag gtagtactag tttccgtcga gacgtccata gaggtggtag   120
atcggaagag cacacgtctg aac                                           143

<210> SEQ ID NO 65
<211> LENGTH: 143
<212> TYPE: DNA
<213> ORGANISM: Artificial Sequence
<220> FEATURE:
```

<223> OTHER INFORMATION: Synthesized

<400> SEQUENCE: 65
tccctacacg acgctcttcc gatctccatc aacaacatga gcacacgtat acttcccttc    60
actaagtgca ctagactgtg ctagatgagc tagtaacatc ggtagcactt tcgacgacag   120
atcggaagag cacacgtctg aac                                           143

<210> SEQ ID NO 66
<211> LENGTH: 143
<212> TYPE: DNA
<213> ORGANISM: Artificial Sequence
<220> FEATURE:
<223> OTHER INFORMATION: Synthesized

<400> SEQUENCE: 66
tccctacacg acgctcttcc gatcttcatc aacaacacgt tgatcactag tcttctcact    60
agctcacgga atctgtcgta gatcatgaca cctcgactac catacttgtg ctcacaacag   120
atcggaagag cacacgtctg aac                                           143

<210> SEQ ID NO 67
<211> LENGTH: 143
<212> TYPE: DNA
<213> ORGANISM: Artificial Sequence
<220> FEATURE:
<223> OTHER INFORMATION: Synthesized

<400> SEQUENCE: 67
tccctacacg acgctcttcc gatctgcatc aacaacacgt aactacccaa gccgaacatt    60
ccacgtagac gatttcagct ctcgtgcaca tctactattc actagttctg gaatctgcag   120
atcggaagag cacacgtctg aac                                           143

<210> SEQ ID NO 68
<211> LENGTH: 143
<212> TYPE: DNA
<213> ORGANISM: Artificial Sequence
<220> FEATURE:
<223> OTHER INFORMATION: Synthesized

<400> SEQUENCE: 68
tccctacacg acgctcttcc gatctctatc aacaacacga ggaggaccta gaatctctca    60
cccaatcgct gctctatctg cttgccctta cccattcaga tgatctcgta catgtagaag   120
atcggaagag cacacgtctg aac                                           143

<210> SEQ ID NO 69
<211> LENGTH: 143
<212> TYPE: DNA
<213> ORGANISM: Artificial Sequence
<220> FEATURE:
<223> OTHER INFORMATION: Synthesized

<400> SEQUENCE: 69
tccctacacg acgctcttcc gatctgtatc aacaacaatc ggagctactt tcagttgcat    60
catcgactgc agatgatgac cacatgacgt agtcagaaag tgatgctacg gatgcagtag   120
atcggaagag cacacgtctg aac                                           143

<210> SEQ ID NO 70
<211> LENGTH: 143
<212> TYPE: DNA
<213> ORGANISM: Artificial Sequence -continued

```
<220> FEATURE:
<223> OTHER INFORMATION: Synthesized

<400> SEQUENCE: 70
tccctacacg acgctcttcc gatctagatc aacaacagga catagataca gtgcagtaat    60
cttcagtcct agcaaggcac gactagtaac tacttcacgt gcagtaatcg attcacagag   120
atcggaagag cacacgtctg aac                                           143

<210> SEQ ID NO 71
<211> LENGTH: 143
<212> TYPE: DNA
<213> ORGANISM: Artificial Sequence
<220> FEATURE:
<223> OTHER INFORMATION: Synthesized

<400> SEQUENCE: 71
tccctacacg acgctcttcc gatctcgatc aacaacattc actaactgac acctcctagt    60
cttccgaaga cgtcacggaa tcccaagttc aaagtgtgca catatcgata gcactcagag   120
atcggaagag cacacgtctg aac                                           143

<210> SEQ ID NO 72
<211> LENGTH: 143
<212> TYPE: DNA
<213> ORGANISM: Artificial Sequence
<220> FEATURE:
<223> OTHER INFORMATION: Synthesized

<400> SEQUENCE: 72
tccctacacg acgctcttcc gatcttgatc aacaacacct actggtgcat gcatcccaca    60
tctaagatga tgcatcatct acgtcagaac acgtgctcta ctctgaagca ctggacacag   120
atcggaagag cacacgtctg aac                                           143

<210> SEQ ID NO 73
<211> LENGTH: 143
<212> TYPE: DNA
<213> ORGANISM: Artificial Sequence
<220> FEATURE:
<223> OTHER INFORMATION: Synthesized

<400> SEQUENCE: 73
tccctacacg acgctcttcc gatctggatc aacaacaaca agttgcccaa tcgacagtag    60
actaggagtc cgatacttct tcagattcgg ttgcacatac gtattcagaa gttgtacaag   120
atcggaagag cacacgtctg aac                                           143

<210> SEQ ID NO 74
<211> LENGTH: 143
<212> TYPE: DNA
<213> ORGANISM: Artificial Sequence
<220> FEATURE:
<223> OTHER INFORMATION: Synthesized

<400> SEQUENCE: 74
tccctacacg acgctcttcc gatctaactc aacaacaagt tgcggactat tcagccgaaa    60
gggtgctatc ctagtattca gaaagtgagc aagaatcgat tctgcaaacc gtatccctag   120
atcggaagag cacacgtctg aac                                           143

<210> SEQ ID NO 75
<211> LENGTH: 143
<212> TYPE: DNA
```

<213> ORGANISM: Artificial Sequence
<220> FEATURE:
<223> OTHER INFORMATION: Synthesized

<400> SEQUENCE: 75

```
tccctacacg acgctcttcc gatctcactc aacaacagca ggatacccat tcagcctacg    60
tcacacacta ccagctagaa agcgtgcagc tgacgtcgct agactatgtc gtactggaag   120
atcggaagag cacacgtctg aac                                           143
```

<210> SEQ ID NO 76
<211> LENGTH: 143
<212> TYPE: DNA
<213> ORGANISM: Artificial Sequence
<220> FEATURE:
<223> OTHER INFORMATION: Synthesized

<400> SEQUENCE: 76

```
tccctacacg acgctcttcc gatcttactc aacaacagct ctagtagtaa gaacatctgc    60
actacaccca gtcctagcc gtcgtgacat cgtacatcct aactacgcta gccagcatag   120
atcggaagag cacacgtctg aac                                           143
```

<210> SEQ ID NO 77
<211> LENGTH: 143
<212> TYPE: DNA
<213> ORGANISM: Artificial Sequence
<220> FEATURE:
<223> OTHER INFORMATION: Synthesized

<400> SEQUENCE: 77

```
tccctacacg acgctcttcc gatctgactc aacaacagta ccaagtactt gaggtcacct    60
ctacggatga agatgatgtg cacacgaccc agctagatga tgaccaacac tcagatgtag   120
atcggaagag cacacgtctg aac                                           143
```

<210> SEQ ID NO 78
<211> LENGTH: 143
<212> TYPE: DNA
<213> ORGANISM: Artificial Sequence
<220> FEATURE:
<223> OTHER INFORMATION: Synthesized

<400> SEQUENCE: 78

```
tccctacacg acgctcttcc gatctatctc aacaacatct catagaaagc gtgcaatcta    60
cgtcagccga ttcaaggctc tactaggtag cagaaactga gcattcgacc tagtactcag   120
atcggaagag cacacgtctg aac                                           143
```

<210> SEQ ID NO 79
<211> LENGTH: 143
<212> TYPE: DNA
<213> ORGANISM: Artificial Sequence
<220> FEATURE:
<223> OTHER INFORMATION: Synthesized

<400> SEQUENCE: 79

```
tccctacacg acgctcttcc gatctctctc aacaacaaga cctaactgtc gtggaatcgg    60
tcatactcta gctggaacat acccacgtag cagttgagca ggaagagtat tcagcctaag   120
atcggaagag cacacgtctg aac                                           143
```

<210> SEQ ID NO 80
<211> LENGTH: 143

```
<212> TYPE: DNA
<213> ORGANISM: Artificial Sequence
<220> FEATURE:
<223> OTHER INFORMATION: Synthesized

<400> SEQUENCE: 80
tccctacacg acgctcttcc gatctttctc aacaacattc agagcttgcg caatcgactg    60
tagatgtagt ggaacaatcg attctagatg tgctgcagac gacctaagta gacagatcag   120
atcggaagag cacacgtctg aac                                           143

<210> SEQ ID NO 81
<211> LENGTH: 143
<212> TYPE: DNA
<213> ORGANISM: Artificial Sequence
<220> FEATURE:
<223> OTHER INFORMATION: Synthesized

<400> SEQUENCE: 81
tccctacacg acgctcttcc gatctgtctc aacaacacat tgaccagtaa tcgtcactag    60
cagctgacac acagacgtcg ctcgatcatg acacccttac tctttctcaa aggtatcaag   120
atcggaagag cacacgtctg aac                                           143

<210> SEQ ID NO 82
<211> LENGTH: 143
<212> TYPE: DNA
<213> ORGANISM: Artificial Sequence
<220> FEATURE:
<223> OTHER INFORMATION: Synthesized

<400> SEQUENCE: 82
tccctacacg acgctcttcc gatctagctc aacaacaagc gcaacatacg atactagaac    60
atgttcaatc tgagtacatc ctctatcttc actagacgat ttcagaacag ctgacggaag   120
atcggaagag cacacgtctg aac                                           143

<210> SEQ ID NO 83
<211> LENGTH: 143
<212> TYPE: DNA
<213> ORGANISM: Artificial Sequence
<220> FEATURE:
<223> OTHER INFORMATION: Synthesized

<400> SEQUENCE: 83
tccctacacg acgctcttcc gatcttgctc aacaacatgc catatcgtaa ctagatcacg    60
tcgtcatatc ggtcctagat gaagttgcga tctaggtagt gtatcaagtg tcgatcgaag   120
atcggaagag cacacgtctg aac                                           143

<210> SEQ ID NO 84
<211> LENGTH: 143
<212> TYPE: DNA
<213> ORGANISM: Artificial Sequence
<220> FEATURE:
<223> OTHER INFORMATION: Synthesized

<400> SEQUENCE: 84
tccctacacg acgctcttcc gatctcattc aacaacagga gacgtcccta ctaacggtcg    60
tcattacgtc ccttcaaact gacactacgg accagctaga agacgtcaca caagacgaag   120
atcggaagag cacacgtctg aac                                           143

<210> SEQ ID NO 85
```

```
<211> LENGTH: 143
<212> TYPE: DNA
<213> ORGANISM: Artificial Sequence
<220> FEATURE:
<223> OTHER INFORMATION: Synthesized

<400> SEQUENCE: 85
tccctacacg acgctcttcc gatctgattc aacaacagac ccacattcaa actgagcaag    60
actagatagc cctacatgag caatctacgc tgtaagatca gcttgcatca tcgtcctcag   120
atcggaagag cacacgtctg aac                                            143

<210> SEQ ID NO 86
<211> LENGTH: 143
<212> TYPE: DNA
<213> ORGANISM: Artificial Sequence
<220> FEATURE:
<223> OTHER INFORMATION: Synthesized

<400> SEQUENCE: 86
tccctacacg acgctcttcc gatctacttc aacaacagac agccctacac gtgcagtact    60
accattcact ctatacgcag taatccattc aagatctcgt cacctactag tccacctcag   120
atcggaagag cacacgtctg aac                                            143

<210> SEQ ID NO 87
<211> LENGTH: 143
<212> TYPE: DNA
<213> ORGANISM: Artificial Sequence
<220> FEATURE:
<223> OTHER INFORMATION: Synthesized

<400> SEQUENCE: 87
tccctacacg acgctcttcc gatctccttc aacaacagat agctgattct gcgcataccc    60
atgaacttga aagggacctc tcgtcttcga tagcgctgca ttcctaccac atacaggaag   120
atcggaagag cacacgtctg aac                                            143

<210> SEQ ID NO 88
<211> LENGTH: 143
<212> TYPE: DNA
<213> ORGANISM: Artificial Sequence
<220> FEATURE:
<223> OTHER INFORMATION: Synthesized

<400> SEQUENCE: 88
tccctacacg acgctcttcc gatcttcttc aacaacagct tgaacatcag tcctaaactg    60
aggacgtcta caccgacctt gacacgtctt cctagacgac gcttgaagat gaggaactag   120
atcggaagag cacacgtctg aac                                            143

<210> SEQ ID NO 89
<211> LENGTH: 143
<212> TYPE: DNA
<213> ORGANISM: Artificial Sequence
<220> FEATURE:
<223> OTHER INFORMATION: Synthesized

<400> SEQUENCE: 89
tccctacacg acgctcttcc gatctgcttc aacaacacgt gatgcaagtt ctgattgtaa    60
gctctacatc actactcgat caaactgaga cgcacagtgc tacgacagtg tacactgcag   120
atcggaagag cacacgtctg aac                                            143
```

<210> SEQ ID NO 90
<211> LENGTH: 143
<212> TYPE: DNA
<213> ORGANISM: Artificial Sequence
<220> FEATURE:
<223> OTHER INFORMATION: Synthesized

<400> SEQUENCE: 90
tccctacacg acgctcttcc gatctagttc aacaacacta agtcagactc accgtgatcg     60
tcctgtaaca tcttacggag cacgaatcca tcagcctatc ctcatctcac atctatgcag    120
atcggaagag cacacgtctg aac                                            143

<210> SEQ ID NO 91
<211> LENGTH: 143
<212> TYPE: DNA
<213> ORGANISM: Artificial Sequence
<220> FEATURE:
<223> OTHER INFORMATION: Synthesized

<400> SEQUENCE: 91
tccctacacg acgctcttcc gatctcgttc aacaacaggt aaggcttgcc acttcctccg     60
aagctacatc ctcgtcccaa caaacgcatt cagctgtact catgacatca acgactgcag    120
atcggaagag cacacgtctg aac                                            143

<210> SEQ ID NO 92
<211> LENGTH: 143
<212> TYPE: DNA
<213> ORGANISM: Artificial Sequence
<220> FEATURE:
<223> OTHER INFORMATION: Synthesized

<400> SEQUENCE: 92
tccctacacg acgctcttcc gatcttgttc aacaacaaag agaccttcta gtcctctccc     60
aagcgtaaag ggagcatgac caatcctctg acctacacca ccaccatgtg gactagctag    120
atcggaagag cacacgtctg aac                                            143

<210> SEQ ID NO 93
<211> LENGTH: 143
<212> TYPE: DNA
<213> ORGANISM: Artificial Sequence
<220> FEATURE:
<223> OTHER INFORMATION: Synthesized

<400> SEQUENCE: 93
tccctacacg acgctcttcc gatctggttc aacaacagta caccgatgac atacactagt     60
cagcgtcgat gctggaggtt ctaagtcagt ccacctcatc cacgcaggta accgttctag    120
atcggaagag cacacgtctg aac                                            143

<210> SEQ ID NO 94
<211> LENGTH: 143
<212> TYPE: DNA
<213> ORGANISM: Artificial Sequence
<220> FEATURE:
<223> OTHER INFORMATION: Synthesized

<400> SEQUENCE: 94
tccctacacg acgctcttcc gatctaagtc aacaacaaga agtggttgca caatcgatgt     60
cagatgatgt gcactcgacg gtgctagaac aggttgccat tacgtaagtt cacgtctcag    120
atcggaagag cacacgtctg aac                                            143

<210> SEQ ID NO 95
<211> LENGTH: 143
<212> TYPE: DNA
<213> ORGANISM: Artificial Sequence
<220> FEATURE:
<223> OTHER INFORMATION: Synthesized

<400> SEQUENCE: 95
tccctacacg acgctcttcc gatctcagtc aacaacaaac gctcaccgaa gaccagctac      60
taactgatgc gtatacgcta gccctaactc tgcaggagac tctcctacta caaagttcag     120
atcggaagag cacacgtctg aac                                             143

<210> SEQ ID NO 96
<211> LENGTH: 143
<212> TYPE: DNA
<213> ORGANISM: Artificial Sequence
<220> FEATURE:
<223> OTHER INFORMATION: Synthesized

<400> SEQUENCE: 96
tccctacacg acgctcttcc gatctacagc aacaacatga ggatcatacc tagctagcag      60
atgagcatgc ctatctccta gatgatgtca ctgcatcgta ttcacaagtg ctagccacag     120
atcggaagag cacacgtctg aac                                             143

<210> SEQ ID NO 97
<211> LENGTH: 143
<212> TYPE: DNA
<213> ORGANISM: Artificial Sequence
<220> FEATURE:
<223> OTHER INFORMATION: Synthesized

<400> SEQUENCE: 97
tccctacacg acgctcttcc gatctccagc aacaacatca atcgacgtcg ctagaacacg      60
ttcactacta ccattcccctt catgagctca tctagaccct ctaagttgag cacattgaag    120
atcggaagag cacacgtctg aac                                             143

<210> SEQ ID NO 98
<211> LENGTH: 143
<212> TYPE: DNA
<213> ORGANISM: Artificial Sequence
<220> FEATURE:
<223> OTHER INFORMATION: Synthesized

<400> SEQUENCE: 98
tccctacacg acgctcttcc gatcttcagc aacaacacct ccagtcagct gcagcgtcgc      60
atcaatcaca tgccgaatca aggcatacct accacatact tactcagcag taccaccaag    120
atcggaagag cacacgtctg aac                                             143

<210> SEQ ID NO 99
<211> LENGTH: 143
<212> TYPE: DNA
<213> ORGANISM: Artificial Sequence
<220> FEATURE:
<223> OTHER INFORMATION: Synthesized

<400> SEQUENCE: 99
tccctacacg acgctcttcc gatctgcagc aacaacagac catcatacta tccgtcgtcc      60
agacgattct ccttgatgag gaactctacc acgaacttgt tgtagcggaa tccctacaag    120
atcggaagag cacacgtctg aac                                             143

<210> SEQ ID NO 100
<211> LENGTH: 143
<212> TYPE: DNA
<213> ORGANISM: Artificial Sequence
<220> FEATURE:
<223> OTHER INFORMATION: Synthesized

<400> SEQUENCE: 100
tccctacacg acgctcttcc gatctctagc aacaacaggt gtacctaagg accgtgatga    60
cgtagcttgc ctaagtgcaa cagacccaag tcctaagtct tgctgaatcg accacagaag   120
atcggaagag cacacgtctg aac                                           143

<210> SEQ ID NO 101
<211> LENGTH: 143
<212> TYPE: DNA
<213> ORGANISM: Artificial Sequence
<220> FEATURE:
<223> OTHER INFORMATION: Synthesized

<400> SEQUENCE: 101
tccctacacg acgctcttcc gatctgtagc aacaacagct ctaagaagtg ctagcatcgt    60
agtcagatga gctgcatacg acggtttcag actacgtcac ccaatctacg tccacctcag   120
atcggaagag cacacgtctg aac                                           143

<210> SEQ ID NO 102
<211> LENGTH: 143
<212> TYPE: DNA
<213> ORGANISM: Artificial Sequence
<220> FEATURE:
<223> OTHER INFORMATION: Synthesized

<400> SEQUENCE: 102
tccctacacg acgctcttcc gatctagagc aacaacaaga catagtgctt acctagtcac    60
tagaagcgac cacgtagacg gtactacttt cagtgtctac gacgatttcc ctggagctag   120
atcggaagag cacacgtctg aac                                           143

<210> SEQ ID NO 103
<211> LENGTH: 143
<212> TYPE: DNA
<213> ORGANISM: Artificial Sequence
<220> FEATURE:
<223> OTHER INFORMATION: Synthesized

<400> SEQUENCE: 103
tccctacacg acgctcttcc gatctcgagc aacaacatct agtgcaacac taccaagcac    60
ttctcgtgga ccactaggtc ctcgatgtgc tcacacacta gctcctagac tagcaagaag   120
atcggaagag cacacgtctg aac                                           143

<210> SEQ ID NO 104
<211> LENGTH: 143
<212> TYPE: DNA
<213> ORGANISM: Artificial Sequence
<220> FEATURE:
<223> OTHER INFORMATION: Synthesized

<400> SEQUENCE: 104
tccctacacg acgctcttcc gatcttgagc aacaacagct cacgtaaaca caagtactaa    60
cgcttgcagc atcccagcta gaaacgctgg agtagaccca gtcagatcaa gtcagcacag   120
atcggaagag cacacgtctg aac                                             143

<210> SEQ ID NO 105
<211> LENGTH: 143
<212> TYPE: DNA
<213> ORGANISM: Artificial Sequence
<220> FEATURE:
<223> OTHER INFORMATION: Synthesized

<400> SEQUENCE: 105
tccctacacg acgctcttcc gatctggagc aacaacacca cactacgtcc gtagatgtgc     60
tggacgagta gtcgtacctt ctcgtccaac agacggtaga actagttgac acggaagaag   120
atcggaagag cacacgtctg aac                                             143

<210> SEQ ID NO 106
<211> LENGTH: 143
<212> TYPE: DNA
<213> ORGANISM: Artificial Sequence
<220> FEATURE:
<223> OTHER INFORMATION: Synthesized

<400> SEQUENCE: 106
tccctacacg acgctcttcc gatctaacgc aacaacaaca gacttcagct gcaagtctcc     60
atcactacat agcagatgaa agcacacagg agcttgcaga acagtgcat cagtcgctag    120 atcggaagag cacacgtctg aac                                             143

<210> SEQ ID NO 107
<211> LENGTH: 143
<212> TYPE: DNA
<213> ORGANISM: Artificial Sequence
<220> FEATURE:
<223> OTHER INFORMATION: Synthesized

<400> SEQUENCE: 107
tccctacacg acgctcttcc gatctcacgc aacaacaaac ggattcactt tctgatgcac     60
actaccatct cctagccacg gagtagacga tagttcaagc caccacctag acgtcgctag   120
atcggaagag cacacgtctg aac                                             143

<210> SEQ ID NO 108
<211> LENGTH: 143
<212> TYPE: DNA
<213> ORGANISM: Artificial Sequence
<220> FEATURE:
<223> OTHER INFORMATION: Synthesized

<400> SEQUENCE: 108
tccctacacg acgctcttcc gatcttacgc aacaacacca catagaagtt gatcagtact     60
accaagttgc ctaagtccaa cactagtatt cagaacatct ttcatcgacg tagacatcag   120
atcggaagag cacacgtctg aac                                             143

<210> SEQ ID NO 109
<211> LENGTH: 143
<212> TYPE: DNA
<213> ORGANISM: Artificial Sequence
<220> FEATURE:
<223> OTHER INFORMATION: Synthesized

<400> SEQUENCE: 109
tccctacacg acgctcttcc gatctgacgc aacaacagct agcagctgtg caaacatctg     60
atctagatga tgacgtacaa tcccagctac ttcaggttgc gacgacggtc ctctacagag   120

```
atcggaagag cacacgtctg aac                                              143

<210> SEQ ID NO 110
<211> LENGTH: 143
<212> TYPE: DNA
<213> ORGANISM: Artificial Sequence
<220> FEATURE:
<223> OTHER INFORMATION: Synthesized

<400> SEQUENCE: 110
tccctacacg acgctcttcc gatctatcgc aacaacaaga acacgtgcag ctgacggaag       60
tcgattcgac gcaaactacg tcgctagctg tggtgcaagc ccaggagtca gagaccgaag      120
atcggaagag cacacgtctg aac                                              143

<210> SEQ ID NO 111
<211> LENGTH: 143
<212> TYPE: DNA
<213> ORGANISM: Artificial Sequence
<220> FEATURE:
<223> OTHER INFORMATION: Synthesized

<400> SEQUENCE: 111
tccctacacg acgctcttcc gatctctcgc aacaacaaag ggtgtctact acggttgcgc       60
actagctgga ttcgacgtac atcctacagg tcactgatac ggaagcccta tcagacagag      120
atcggaagag cacacgtctg aac                                              143

<210> SEQ ID NO 112
<211> LENGTH: 143
<212> TYPE: DNA
<213> ORGANISM: Artificial Sequence
<220> FEATURE:
<223> OTHER INFORMATION: Synthesized

<400> SEQUENCE: 112
tccctacacg acgctcttcc gatctttcgc aacaacagct cgtacatacg atcatagcct       60
aagtggagat tacctaccta gaaacagtca ctcttacgta ctaactaact gacctctaag      120
atcggaagag cacacgtctg aac                                              143

<210> SEQ ID NO 113
<211> LENGTH: 143
<212> TYPE: DNA
<213> ORGANISM: Artificial Sequence
<220> FEATURE:
<223> OTHER INFORMATION: Synthesized

<400> SEQUENCE: 113
tccctacacg acgctcttcc gatctgtcgc aacaacacgt ccaggacatt tcagaatcca       60
ccacacagta gtattcagaa actgtcgttg cctacatgct cgaaagcgtg cagacgacag      120
atcggaagag cacacgtctg aac                                              143

<210> SEQ ID NO 114
<211> LENGTH: 143
<212> TYPE: DNA
<213> ORGANISM: Artificial Sequence
<220> FEATURE:
<223> OTHER INFORMATION: Synthesized

<400> SEQUENCE: 114
tccctacacg acgctcttcc gatctagcgc aacaacaagc atcccattcc cttcatgtaa       60
```
catcctctct gctagatgat gatgcgtata cccattccga aaccgtcacc catctagaag    120
atcggaagag cacacgtctg aac                                           143

<210> SEQ ID NO 115
<211> LENGTH: 143
<212> TYPE: DNA
<213> ORGANISM: Artificial Sequence
<220> FEATURE:
<223> OTHER INFORMATION: Synthesized

<400> SEQUENCE: 115
tccctacacg acgctcttcc gatcttgcgc aacaacatac tacagcagac tacgtgctta    60
catcgtattc cgaagctgag caactatcga cagcctaagc cgttgcgtag acaacctcag   120
atcggaagag cacacgtctg aac                                           143

<210> SEQ ID NO 116
<211> LENGTH: 143
<212> TYPE: DNA
<213> ORGANISM: Artificial Sequence
<220> FEATURE:
<223> OTHER INFORMATION: Synthesized

<400> SEQUENCE: 116
tccctacacg acgctcttcc gatctcatgc aacaacagta ttccctagct gttgcacaga    60
cgtcagcgta tgatgtgcat acgacccagc tagatgttga tgccgagact ctttcaagag   120
atcggaagag cacacgtctg aac                                           143

<210> SEQ ID NO 117
<211> LENGTH: 143
<212> TYPE: DNA
<213> ORGANISM: Artificial Sequence
<220> FEATURE:
<223> OTHER INFORMATION: Synthesized

<400> SEQUENCE: 117
tccctacacg acgctcttcc gatctgatgc aacaacaact cgaaaccgtg ctatctacgt    60
aagcacttga tgagctcatt acgtaagtag aagctctgca gactacgctt tctctgctag   120
atcggaagag cacacgtctg aac                                           143

<210> SEQ ID NO 118
<211> LENGTH: 143
<212> TYPE: DNA
<213> ORGANISM: Artificial Sequence
<220> FEATURE:
<223> OTHER INFORMATION: Synthesized

<400> SEQUENCE: 118
tccctacacg acgctcttcc gatctactgc aacaacaact acacgtgtca catacgtacc    60
tacttcaagt gcaacagacg tacgttcaag cggtcacctc gacgatagta gaacaactag   120
atcggaagag cacacgtctg aac                                           143

<210> SEQ ID NO 119
<211> LENGTH: 143
<212> TYPE: DNA
<213> ORGANISM: Artificial Sequence
<220> FEATURE:
<223> OTHER INFORMATION: Synthesized

<400> SEQUENCE: 119
tccctacacg acgctcttcc gatctcctgc aacaacaatc gatcctagta gccagagaga    60
cgatactcat ccagcagtcc ctcagcacga ctctttctac cagcgtagtg atccagctag    120
atcggaagag cacacgtctg aac                                            143

<210> SEQ ID NO 120
<211> LENGTH: 143
<212> TYPE: DNA
<213> ORGANISM: Artificial Sequence
<220> FEATURE:
<223> OTHER INFORMATION: Synthesized

<400> SEQUENCE: 120
tccctacacg acgctcttcc gatcttctgc aacaacaagt aagctcgcac caggaaacgt     60
cgacagacag gaccatagag atctcacagg agtagctcag gactcatctt cacgtcacag    120
atcggaagag cacacgtctg aac                                            143

<210> SEQ ID NO 121
<211> LENGTH: 143
<212> TYPE: DNA
<213> ORGANISM: Artificial Sequence
<220> FEATURE:
<223> OTHER INFORMATION: Synthesized

<400> SEQUENCE: 121
tccctacacg acgctcttcc gatctgctgc aacaacaagt atcagtgcta gtcacctact     60
ccgtcgtcgt cctggttaca agtcaaaggt aatcaagaga aactgtccac ctccacgaag    120
atcggaagag cacacgtctg aac                                            143

<210> SEQ ID NO 122
<211> LENGTH: 143
<212> TYPE: DNA
<213> ORGANISM: Artificial Sequence
<220> FEATURE:
<223> OTHER INFORMATION: Synthesized

<400> SEQUENCE: 122
tccctacacg acgctcttcc gatctagtgc aacaacagtc cactctgaca gcttcaagtg     60
tcgacataag ggagctcgtc tcaagcactg ctacggagga agagacagaa acccaggaag    120
atcggaagag cacacgtctg aac                                            143

<210> SEQ ID NO 123
<211> LENGTH: 143
<212> TYPE: DNA
<213> ORGANISM: Artificial Sequence
<220> FEATURE:
<223> OTHER INFORMATION: Synthesized

<400> SEQUENCE: 123
tccctacacg acgctcttcc gatctcgtgc aacaacagct atcacaaact gccgtcactc     60
aagtagtcag ctaacataca acgaccgata cggagtccag atccctcgtc ctcgtagaag    120
atcggaagag cacacgtctg aac                                            143

<210> SEQ ID NO 124
<211> LENGTH: 143
<212> TYPE: DNA
<213> ORGANISM: Artificial Sequence
<220> FEATURE:
<223> OTHER INFORMATION: Synthesized

<400> SEQUENCE: 124
tccctacacg acgctcttcc gatcttgtgc aacaacatgt ctatgcactc ctcgaagtca    60
ctgaactact aagagtcgtt gagcagtcct atgtggacta tacagtgcac gatcttcaag    120
atcggaagag cacacgtctg aac    143

<210> SEQ ID NO 125
<211> LENGTH: 143
<212> TYPE: DNA
<213> ORGANISM: Artificial Sequence
<220> FEATURE:
<223> OTHER INFORMATION: Synthesized

<400> SEQUENCE: 125
tccctacacg acgctcttcc gatctggtgc aacaacaaac tgatgcccag acgtccatag    60
atgatcttgc tgactaccag ctcgaaacgc ttgcgacgac ggagctacta cacactacag    120
atcggaagag cacacgtctg aac    143

<210> SEQ ID NO 126
<211> LENGTH: 143
<212> TYPE: DNA
<213> ORGANISM: Artificial Sequence
<220> FEATURE:
<223> OTHER INFORMATION: Synthesized

<400> SEQUENCE: 126
tccctacacg acgctcttcc gatctaaggc aacaacacgt gcactcgacg tatgtagact    60
acgtcacgta tacccattca gaagctgacg tatctacgct cctagactat gctacgtaag    120
atcggaagag cacacgtctg aac    143

<210> SEQ ID NO 127
<211> LENGTH: 143
<212> TYPE: DNA
<213> ORGANISM: Artificial Sequence
<220> FEATURE:
<223> OTHER INFORMATION: Synthesized

<400> SEQUENCE: 127
tccctacacg acgctcttcc gatctcaggc aacaacatgc atcatcgctt ctagcaacgg    60
tgctatctac catcatactt catgagcaga tgaccatttc actagtcgtc gtggagatag    120
atcggaagag cacacgtctg aac    143

<210> SEQ ID NO 128
<211> LENGTH: 143
<212> TYPE: DNA
<213> ORGANISM: Artificial Sequence
<220> FEATURE:
<223> OTHER INFORMATION: Synthesized

<400> SEQUENCE: 128
tccctacacg acgctcttcc gatctacact aacaacacat tactgatgcc gaacatgaca    60
cacatacgta ttcacttgtg gtgcacatta cggtttcact tgttctgcag caagctgaag    120
atcggaagag cacacgtctg aac    143

<210> SEQ ID NO 129
<211> LENGTH: 143
<212> TYPE: DNA
<213> ORGANISM: Artificial Sequence
<220> FEATURE:
<223> OTHER INFORMATION: Synthesized

<400> SEQUENCE: 129
tccctacacg acgctcttcc gatctccact aacaacagac gtattccctt gacgtgcaca    60
ttacggtagt agatctagtg caagcgacgt aagtgcatct gctcacggaa tcgctaacag   120
atcggaagag cacacgtctg aac                                           143

<210> SEQ ID NO 130
<211> LENGTH: 143
<212> TYPE: DNA
<213> ORGANISM: Artificial Sequence
<220> FEATURE:
<223> OTHER INFORMATION: Synthesized

<400> SEQUENCE: 130
tccctacacg acgctcttcc gatcttcact aacaacagta agtcgaaact gatgcttcct    60
aggaagtaga agacgttgcg tatacccatg cacttcatgt gcttactacg tcctattcag   120
atcggaagag cacacgtctg aac                                           143

<210> SEQ ID NO 131
<211> LENGTH: 143
<212> TYPE: DNA
<213> ORGANISM: Artificial Sequence
<220> FEATURE:
<223> OTHER INFORMATION: Synthesized

<400> SEQUENCE: 131
tccctacacg acgctcttcc gatctgcact aacaacagct agatgatctg caccaatccc    60
aagcactaac cgtgcaccag acgatagcac ttgttacgct tacctagacc ctcatagcag   120
atcggaagag cacacgtctg aac                                           143

<210> SEQ ID NO 132
<211> LENGTH: 143
<212> TYPE: DNA
<213> ORGANISM: Artificial Sequence
<220> FEATURE:
<223> OTHER INFORMATION: Synthesized

<400> SEQUENCE: 132
tccctacacg acgctcttcc gatctctact aacaacaaga agcagtcacc ctgacgatac    60
tagctctgct cgtggactag tcttcagcaa ctctccaaca ctaccattca ctaagcacag   120
atcggaagag cacacgtctg aac                                           143

<210> SEQ ID NO 133
<211> LENGTH: 143
<212> TYPE: DNA
<213> ORGANISM: Artificial Sequence
<220> FEATURE:
<223> OTHER INFORMATION: Synthesized

<400> SEQUENCE: 133
tccctacacg acgctcttcc gatctgtact aacaacaaac ggtgcacgat acgatgtcag    60
aacacaccca gacatcccat gtactacaca ccgtagcgac ccagctcctc tacacagaag   120
atcggaagag cacacgtctg aac                                           143

<210> SEQ ID NO 134
<211> LENGTH: 143
<212> TYPE: DNA
<213> ORGANISM: Artificial Sequence
<220> FEATURE:
<223> OTHER INFORMATION: Synthesized

<400> SEQUENCE: 134
tccctacacg acgctcttcc gatctagact aacaacacgt tgcgtatacg taagcagatc    60
aagtgtcaca gacgtcgtca gctgaagcgt cgtactaggt ttcccttgag ctgatcctag   120
atcggaagag cacacgtctg aac                                          143

<210> SEQ ID NO 135
<211> LENGTH: 143
<212> TYPE: DNA
<213> ORGANISM: Artificial Sequence
<220> FEATURE:
<223> OTHER INFORMATION: Synthesized

<400> SEQUENCE: 135
tccctacacg acgctcttcc gatctcgact aacaacagca gtactacatg ctacttctgg    60
tcgtacaatc gatagcacta catgacgtac atacccatgc actaacagtc acctaagcag   120
atcggaagag cacacgtctg aac                                          143

<210> SEQ ID NO 136
<211> LENGTH: 143
<212> TYPE: DNA
<213> ORGANISM: Artificial Sequence
<220> FEATURE:
<223> OTHER INFORMATION: Synthesized

<400> SEQUENCE: 136
tccctacacg acgctcttcc gatcttgact aacaacagct ctaccaccta gctgaagtgc    60
aatcggagac cctcctaagt ctgcactcgg attcccttca tgttgtcaca gcagacgaag   120
atcggaagag cacacgtctg aac                                          143

<210> SEQ ID NO 137
<211> LENGTH: 143
<212> TYPE: DNA
<213> ORGANISM: Artificial Sequence
<220> FEATURE:
<223> OTHER INFORMATION: Synthesized

<400> SEQUENCE: 137
tccctacacg acgctcttcc gatctggact aacaacacta ccagtatcaa catgacacgt    60
agacgtacct actctaggtc acccaatcgt attcactaca gctgcactcc tatgtatcag   120
atcggaagag cacacgtctg aac                                          143

<210> SEQ ID NO 138
<211> LENGTH: 143
<212> TYPE: DNA
<213> ORGANISM: Artificial Sequence
<220> FEATURE:
<223> OTHER INFORMATION: Synthesized

<400> SEQUENCE: 138
tccctacacg acgctcttcc gatctaacct aacaacacca gctactacaa gtgcagcaat    60
cggtagtagc tgttctcaca tcgacggaag tagatacagc ccattcgaca cagctggaag   120
atcggaagag cacacgtctg aac                                          143

<210> SEQ ID NO 139
<211> LENGTH: 143
<212> TYPE: DNA
<213> ORGANISM: Artificial Sequence
<220> FEATURE:
<223> OTHER INFORMATION: Synthesized

<400> SEQUENCE: 139
tccctacacg acgctcttcc gatctcacct aacaacacct actaaggatc acccatactg    60
acgttcaaca tgacactact acgctagctc aagctgacgt acagactctt gtcgaccaag   120
atcggaagag cacacgtctg aac                                           143

<210> SEQ ID NO 140
<211> LENGTH: 143
<212> TYPE: DNA
<213> ORGANISM: Artificial Sequence
<220> FEATURE:
<223> OTHER INFORMATION: Synthesized

<400> SEQUENCE: 140
tccctacacg acgctcttcc gatcttacct aacaacaaga agatgtgcaa tctacgtatt    60
cactacaggt gcacattact tcagcactac acgtgcagga gacggtttca gcggagatag   120
atcggaagag cacacgtctg aac                                           143

<210> SEQ ID NO 141
<211> LENGTH: 143
<212> TYPE: DNA
<213> ORGANISM: Artificial Sequence
<220> FEATURE:
<223> OTHER INFORMATION: Synthesized

<400> SEQUENCE: 141
tccctacacg acgctcttcc gatctgacct aacaacaaac tgttgctgag acgctagtag    60
atgtggtgca ttctacttct tctcatcagg tgtccatgac gtagctagat ctcgtctcag   120
atcggaagag cacacgtctg aac                                           143

<210> SEQ ID NO 142
<211> LENGTH: 143
<212> TYPE: DNA
<213> ORGANISM: Artificial Sequence
<220> FEATURE:
<223> OTHER INFORMATION: Synthesized

<400> SEQUENCE: 142
tccctacacg acgctcttcc gatctatcct aacaacaggt tgcgtatacg taagtagaag    60
atgacgttga taccatttca gaacacgtcg tacagacgct agtacttgat gaagattcag   120
atcggaagag cacacgtctg aac                                           143

<210> SEQ ID NO 143
<211> LENGTH: 143
<212> TYPE: DNA
<213> ORGANISM: Artificial Sequence
<220> FEATURE:
<223> OTHER INFORMATION: Synthesized

<400> SEQUENCE: 143
tccctacacg acgctcttcc gatctctcct aacaacagct ggataccata gtagaagctc    60
tgcaccatac gatttcagaa acggtgtccc aaacccatgc cgaaactctc caagcggtag   120
atcggaagag cacacgtctg aac                                           143

<210> SEQ ID NO 144
<211> LENGTH: 143
<212> TYPE: DNA
<213> ORGANISM: Artificial Sequence
<220> FEATURE:

<223> OTHER INFORMATION: Synthesized

<400> SEQUENCE: 144
tccctacacg acgctcttcc gatctttcct aacaacaaca atcgtattca gaaaccgtca      60
cccaatcgta cctagatcat ctcgtacaat cgctagcagc agagctcacg tcttcggaag     120
atcggaagag cacacgtctg aac                                             143

<210> SEQ ID NO 145
<211> LENGTH: 143
<212> TYPE: DNA
<213> ORGANISM: Artificial Sequence
<220> FEATURE:
<223> OTHER INFORMATION: Synthesized

<400> SEQUENCE: 145
tccctacacg acgctcttcc gatctgtcct aacaacatac ccacctcgaa gctgtcgtga      60
catctacagt cctagctctc acagcgacta ccctagcaca tgaccacata gagtagcaag     120
atcggaagag cacacgtctg aac                                             143

<210> SEQ ID NO 146
<211> LENGTH: 143
<212> TYPE: DNA
<213> ORGANISM: Artificial Sequence
<220> FEATURE:
<223> OTHER INFORMATION: Synthesized

<400> SEQUENCE: 146
tccctacacg acgctcttcc gatctagcct aacaacagta agttcaagat ctgtcatcta      60
ctacttctca acacgtcgtt gcgacgtctt cactacacat gcaacatact tcatccacag     120
atcggaagag cacacgtctg aac                                             143

<210> SEQ ID NO 147
<211> LENGTH: 143
<212> TYPE: DNA
<213> ORGANISM: Artificial Sequence
<220> FEATURE:
<223> OTHER INFORMATION: Synthesized

<400> SEQUENCE: 147
tccctacacg acgctcttcc gatcttgcct aacaacacct tcaacatctc acacagtaca      60
tttcagaaca cgtgtcgcag acgtattcag atctttccgt agaatccata gtcactgaag     120
atcggaagag cacacgtctg aac                                             143

<210> SEQ ID NO 148
<211> LENGTH: 143
<212> TYPE: DNA
<213> ORGANISM: Artificial Sequence
<220> FEATURE:
<223> OTHER INFORMATION: Synthesized

<400> SEQUENCE: 148
tccctacacg acgctcttcc gatctcatct aacaacaaga acacgtcgtt acatcttctt      60
cagaagaggt gcaacaatcg taagtacttc aggtcacgta gacccaactg cagctgtaag     120
atcggaagag cacacgtctg aac                                             143

<210> SEQ ID NO 149
<211> LENGTH: 143
<212> TYPE: DNA
<213> ORGANISM: Artificial Sequence

```
<220> FEATURE:
<223> OTHER INFORMATION: Synthesized

<400> SEQUENCE: 149
tccctacacg acgctcttcc gatctgatct aacaacatga gctgcaagcg acgtcttccg    60
attctgtgca gtagacgata ctagatgtcg tcacatcgac ggtagttcat acagacgtag   120
atcggaagag cacacgtctg aac                                           143

<210> SEQ ID NO 150
<211> LENGTH: 143
<212> TYPE: DNA
<213> ORGANISM: Artificial Sequence
<220> FEATURE:
<223> OTHER INFORMATION: Synthesized

<400> SEQUENCE: 150
tccctacacg acgctcttcc gatctactct aacaacacca caccctgtcg caaagcgaga    60
tgaccgtggt ctaactcctc aggtatcatg attcgcaggt agttgaactc gagacctaag   120
atcggaagag cacacgtctg aac                                           143

<210> SEQ ID NO 151
<211> LENGTH: 143
<212> TYPE: DNA
<213> ORGANISM: Artificial Sequence
<220> FEATURE:
<223> OTHER INFORMATION: Synthesized

<400> SEQUENCE: 151
tccctacacg acgctcttcc gatctcctct aacaacatgt cagtcagctg caggtccacc    60
ttgtccatca cagcgatctt gtggtgactc tgacatcgac tcatacccctc acagttgaag  120 atcggaagag cacacgtctg aac                                           143

<210> SEQ ID NO 152
<211> LENGTH: 143
<212> TYPE: DNA
<213> ORGANISM: Artificial Sequence
<220> FEATURE:
<223> OTHER INFORMATION: Synthesized

<400> SEQUENCE: 152
tccctacacg acgctcttcc gatcttctct aacaacaact ggaggtctag cacctaactg    60
cgctactgtc cgtgtacact tcagctctgg tcattgacgt agagcttgtc tatgtcatag   120
atcggaagag cacacgtctg aac                                           143

<210> SEQ ID NO 153
<211> LENGTH: 143
<212> TYPE: DNA
<213> ORGANISM: Artificial Sequence
<220> FEATURE:
<223> OTHER INFORMATION: Synthesized

<400> SEQUENCE: 153
tccctacacg acgctcttcc gatctgctct aacaacatgc tcatcttaca aggactgaca    60
caactacaca tgaccaggtc catcacagca gcacaagatc aagcataact accgtgatag   120
atcggaagag cacacgtctg aac                                           143

<210> SEQ ID NO 154
<211> LENGTH: 143
<212> TYPE: DNA
```

<213> ORGANISM: Artificial Sequence
<220> FEATURE:
<223> OTHER INFORMATION: Synthesized

<400> SEQUENCE: 154

```
tccctacacg acgctcttcc gatctagtct aacaacaagc atcctaccat gcccttcttt    60
catcaacatc gtatgtcagg cagtctacgg tagcagcagc gatactatcc cactcgatag   120
atcggaagag cacacgtctg aac                                           143
```

<210> SEQ ID NO 155
<211> LENGTH: 143
<212> TYPE: DNA
<213> ORGANISM: Artificial Sequence
<220> FEATURE:
<223> OTHER INFORMATION: Synthesized

<400> SEQUENCE: 155

```
tccctacacg acgctcttcc gatctcgtct aacaacaaca ttccgtccat gacgtttcgc    60
ttgcagtctc gataaggacg tagacagacg tagtcgacct cagccatact actctcgtag   120
atcggaagag cacacgtctg aac                                           143
```

<210> SEQ ID NO 156
<211> LENGTH: 143
<212> TYPE: DNA
<213> ORGANISM: Artificial Sequence
<220> FEATURE:
<223> OTHER INFORMATION: Synthesized

<400> SEQUENCE: 156

```
tccctacacg acgctcttcc gatcttgtct aacaacacac ccaacagacg tagctagcac    60
acgttgcctc atctgtttcc tattctctca catctacggt agtacttctt gattctcaag   120
atcggaagag cacacgtctg aac                                           143
```

<210> SEQ ID NO 157
<211> LENGTH: 143
<212> TYPE: DNA
<213> ORGANISM: Artificial Sequence
<220> FEATURE:
<223> OTHER INFORMATION: Synthesized

<400> SEQUENCE: 157

```
tccctacacg acgctcttcc gatctggtct aacaacatca ctatacgtat gtagcacaag    60
tcacatccta ccaggaacta agggtcacca tgacacattc ctaactcgtc gtggatacag   120
atcggaagag cacacgtctg aac                                           143
```

<210> SEQ ID NO 158
<211> LENGTH: 143
<212> TYPE: DNA
<213> ORGANISM: Artificial Sequence
<220> FEATURE:
<223> OTHER INFORMATION: Synthesized

<400> SEQUENCE: 158

```
tccctacacg acgctcttcc gatctaagct aacaacaagc tacgatttca gctgttgatc    60
acatgaccca agcagcacat tccacatcga cgctttcact tcttgtgcta caactatcag   120
atcggaagag cacacgtctg aac                                           143
```

<210> SEQ ID NO 159
<211> LENGTH: 143

<212> TYPE: DNA
<213> ORGANISM: Artificial Sequence
<220> FEATURE:
<223> OTHER INFORMATION: Synthesized

<400> SEQUENCE: 159
tccctacacg acgctcttcc gatctcagct aacaacaatc ccaactagat catctcgtgt      60
actaccacat ccttgatgtg ctacagacgt acctcgatac gctcacatca tcgatatcag    120
atcggaagag cacacgtctg aac                                             143

<210> SEQ ID NO 160
<211> LENGTH: 143
<212> TYPE: DNA
<213> ORGANISM: Artificial Sequence
<220> FEATURE:
<223> OTHER INFORMATION: Synthesized

<400> SEQUENCE: 160
tccctacacg acgctcttcc gatctacagt aacaacagtc catactaagc gtgtcacaat      60
cgtccctagc acaggtgcat gataccattt cgcactagac caccatgaca cagatctaag    120
atcggaagag cacacgtctg aac                                             143

<210> SEQ ID NO 161
<211> LENGTH: 143
<212> TYPE: DNA
<213> ORGANISM: Artificial Sequence
<220> FEATURE:
<223> OTHER INFORMATION: Synthesized

<400> SEQUENCE: 161
tccctacacg acgctcttcc gatctccagt aacaacattc cgaagcgctc acccaatctg      60
attcagaaag gctgtcacaa acgacagcac tcatcgtcgt atctactgtt gctgagcaag    120
atcggaagag cacacgtctg aac                                             143

<210> SEQ ID NO 162
<211> LENGTH: 143
<212> TYPE: DNA
<213> ORGANISM: Artificial Sequence
<220> FEATURE:
<223> OTHER INFORMATION: Synthesized

<400> SEQUENCE: 162
tccctacacg acgctcttcc gatcttcagt aacaacacct agatgagcaa gctacgatca      60
tactatccgt gtctacctac cagtcactaa gtgttgcagc tacgatgctc ctctacctag    120
atcggaagag cacacgtctg aac                                             143

<210> SEQ ID NO 163
<211> LENGTH: 143
<212> TYPE: DNA
<213> ORGANISM: Artificial Sequence
<220> FEATURE:
<223> OTHER INFORMATION: Synthesized

<400> SEQUENCE: 163
tccctacacg acgctcttcc gatctgcagt aacaacaaca cgtcgtatct acgtccatac      60
ttgtgctgct acaatcgtcc ctagcacata cggacataga ttcgctagca gtgtctacag    120
atcggaagag cacacgtctg aac                                             143

<210> SEQ ID NO 164

```
<211> LENGTH: 143
<212> TYPE: DNA
<213> ORGANISM: Artificial Sequence
<220> FEATURE:
<223> OTHER INFORMATION: Synthesized

<400> SEQUENCE: 164
tccctacacg acgctcttcc gatctctagt aacaacatac ggacatagat tcagttcatg      60
ttcattcaac ccacatgtaa caacaacaac aacaacaaca acaacaacaa cacgtcagag     120
atcggaagag cacacgtctg aac                                             143

<210> SEQ ID NO 165
<211> LENGTH: 143
<212> TYPE: DNA
<213> ORGANISM: Artificial Sequence
<220> FEATURE:
<223> OTHER INFORMATION: Synthesized

<400> SEQUENCE: 165
tccctacacg acgctcttcc gatctgtagt aacaacaggt ctcgtcgcaa gcgcaagcct      60
atgcatccag ggatcattct cttgcttcca gcgtagcgac gcaaacagac cactacatag     120
atcggaagag cacacgtctg aac                                             143

<210> SEQ ID NO 166
<211> LENGTH: 143
<212> TYPE: DNA
<213> ORGANISM: Artificial Sequence
<220> FEATURE:
<223> OTHER INFORMATION: Synthesized

<400> SEQUENCE: 166
tccctacacg acgctcttcc gatctagagt aacaacattc gtatgttgct gaatcatctg      60
actacgttgc agaagctcac cttgctgttg ccattcaatc gtcaaggtat gaactcctag     120
atcggaagag cacacgtctg aac                                             143
```